United States Patent
Alvaro et al.

(10) Patent No.: US 7,214,680 B2
(45) Date of Patent: May 8, 2007

(54) 2-SUBSTITUTED 1-ARYLPIPERAZINES AS TACHYKININ ANTAGONISTS AND/OR SEROTONIN REUPTAKE INHIBITORS

(75) Inventors: Giuseppe Alvaro, Verona (IT); Torquil I. M. Jack, Stevenage (GB); Maria Elvira Tranquillini, Verona (IT)

(73) Assignee: Glaxo Group Limited (GB)

( * ) Notice: Subject to any disclaimer, the term of this patent is extended or adjusted under 35 U.S.C. 154(b) by 369 days.

(21) Appl. No.: 10/486,479

(22) PCT Filed: Aug. 13, 2002

(86) PCT No.: PCT/EP02/09066

§ 371 (c)(1),
(2), (4) Date: Jul. 7, 2004

(87) PCT Pub. No.: WO03/015784

PCT Pub. Date: Feb. 27, 2003

(65) Prior Publication Data

US 2004/0242592 A1    Dec. 2, 2004

(30) Foreign Application Priority Data

Aug. 14, 2001 (GB) .................. 0119797.9

(51) Int. Cl.
*A61K 31/495* (2006.01)
*C07D 241/04* (2006.01)

(52) U.S. Cl. .................. 514/255.01; 544/393
(58) Field of Classification Search .................. 544/393
See application file for complete search history.

(56) References Cited

U.S. PATENT DOCUMENTS

| 5,607,936 A | 3/1997 | Yuan-Ching et al. |
| 5,880,128 A | 3/1999 | Doll et al. |
| 6,642,240 B2 | 11/2003 | Alvaro et al. |

FOREIGN PATENT DOCUMENTS

| EP | 0 464 604 | 1/1992 |
| WO | WO-9525443 A1 | 9/1995 |
| WO | WO-9631501 A1 | 10/1996 |
| WO | WO-9723466 A1 | 7/1997 |
| WO | WO-9846626 A1 | 10/1998 |
| WO | WO-9846627 A1 | 10/1998 |
| WO | WO 01 25219 | 4/2001 |
| WO | WO 01/25219 | 4/2001 |
| WO | WO 02/32867 | 4/2002 |

OTHER PUBLICATIONS

Ohnmacht et al. in Annual Reports in Medicinal Chemistry, vol. 33, p. 71-80 (1998).*
Robichaud et al. in Annual Reports in Medicinal Chemistry, vol. 35, p. 11-20 (2000).*
Vippagunta et al. Advanced Drug Delivery Reviews, vol. 48, p. 3-26 (2001).*
Tamiz, A.P., et al. "A Convenient Procedure for the Synthesis of Nonsymmetrical Bivalent Selective Seronine Reuptake Inhibitors Using Polymer-Supported Reagents." Biorg. Med. Chem. Lett., vol. 10, No. 24, 2000, pp. 2741-2744.

* cited by examiner

*Primary Examiner*—Emily Bernhardt
(74) *Attorney, Agent, or Firm*—Lorie Ann Morgan

(57) ABSTRACT

The present invention relates to piperazine of formula (I)

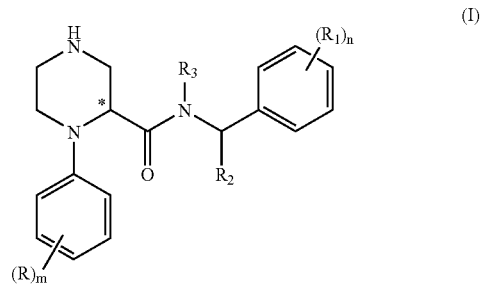

wherein
R represents halogen, $C_{1-4}$ alkyl, trifluoromethoxy or trifluoromethyl;
$R_1$ is trifluoromethyl, $C_{1-4}$ alkyl, $C_{1-4}$ alkoxy, halogen or trifluoromethoxy;
$R_2$ is hydrogen, $C_{1-4}$ alkyl or $C_{2-6}$ alkenyl;
$R_3$ represents hydrogen or $C_{1-4}$ alkyl;
n and m are independently 0 or an integer from 1 to 3;
and pharmaceutically acceptable salts and solvates thereof, process for their preparation and their use in the treatment of condition mediated by tachykinins and/or by selective inhibition of the serotonin reuptake transporter protein.

15 Claims, No Drawings

2-SUBSTITUTED 1-ARYLPIPERAZINES AS TACHYKININ ANTAGONISTS AND/OR SEROTONIN REUPTAKE INHIBITORS

CROSS REFERENCES TO RELATED APPLICATIONS

This application is a 371 Application of PCT/EP02/09066. filed 13 Aug. 2002, which claims priority to GB Application Serial No. 0119797.9, filed 14 Aug. 2001.

The present invention relates to N-phenyl piperazine derivatives, to processes for their preparation, to pharmaceutical compositions containing them and to their medical use.

U.S. Pat. No. 5,880,128 and WO 9631501 disclose interalia N'-carbonyl-N aryl piperazine derivatives which inhibit farnesylprotein transferase.

WO 9846626 and WO 9846627 disclose some N-phenyl-N' substituted piperazine derivatives as factor Xa inhibitors. Such compounds are useful as inhibitors of blood coagulation in mammalian species.

WO 9525443 describes certain N-phenyl-N' substituted piperazine derivatives useful as oxytocin or vasopressin antagonists.

However in the above cited documents there is neither disclosure nor suggestion of any compound as claimed herein.

Thus the present invention provides compounds of formula (I)

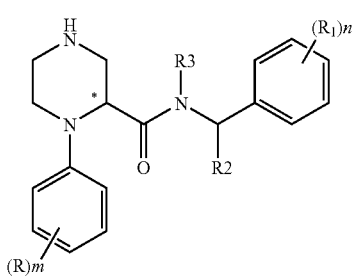

(I)

wherein
R represents halogen, $C_{1-4}$ alkyl, trifluoromethoxy or trifluoromethyl;
$R_1$ is trifluoromethyl, $C_{1-4}$ alkyl, $C_{1-4}$ alkoxy, halogen or trifluoromethoxy;
$R_2$ is hydrogen, $C_{1-4}$ alkyl or $C_{2-6}$ alkenyl;
$R_3$ represents hydrogen or $C_{1-4}$ alkyl;
n and m are independently 0 or an integer from 1 to 3;
and pharmaceutically acceptable salts and solvates thereof.

A further embodiment of the invention provides compounds of formula (I) and pharmaceutically acceptable salts and solvates thereof, wherein
R represents halogen or $C_{1-4}$ alkyl;
$R_1$ is trifluoromethyl, $C_{1-4}$ alkyl, $C_{1-4}$ alkoxy, halogen or trifluoromethoxy;
$R_2$ is hydrogen, $C_{1-4}$ alkyl or $C_{2-6}$ alkenyl;
$R_3$ represents hydrogen or $C_{1-4}$ alkyl;
n and m are independently 0 or an integer from 1 to 3;
Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, trifluoroacetates, lactates, fumarates, malates and maleates.

The solvates may, for example, be hydrates.

References hereinafter to a compound according to the invention include both compounds of formula (I) and their pharmaceutically acceptable acid addition salts together with pharmaceutically acceptable solvates.

It will be appreciated by those skilled in the art that the compounds of formula (I) contain at least one chiral centre (namely the carbon atom shown as * in formula (I)) and these may be represented by the formulae (1a) and (1b)

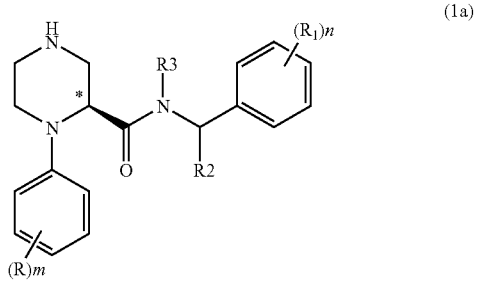

(1a)

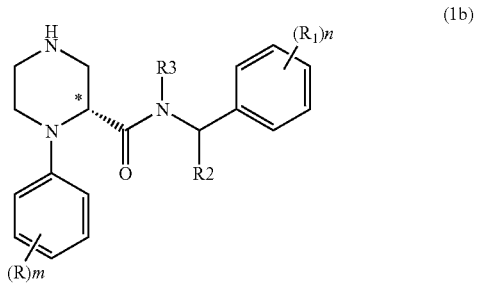

(1b)

The wedge shaped bond indicates that the bond is above the plane of the paper. The broken bond indicates that the bond is below the plane of the paper.

The configuration shown for the chiral carbon atom indicated as * in formula 1a is β and in formula 1b is α

In general, in the specific compounds named below, the β configuration at the chiral carbon atom indicated as * corresponds to the S isomer and the α configuration corresponds to the R isomer.

Further asymmetric carbon atoms are possible in the compound of formula (I). Thus, for example, when $R_2$ is $C_{1-4}$ alkyl or $C_{2-6}$ alkenyl, the compounds of formula (I) possess at least two asymmetric carbon atoms.

The assignment of the R and S configuration of the asymmetric carbon atoms of the compounds of the invention has been made according to the rules of Cahn, Ingold and Prelog 1956, 12, 81.

It is to be understood that all stereoisomeric forms, including all enantiomers, diastereoisomers and all mixtures thereof, including racemates, are encompassed within the scope of the present invention and the reference to compounds of formula (I) includes all stereoisomeric forms unless otherwise stated.

Furthermore, some of the crystalline forms of the compounds of structure (I) may exist as polymorphs, which are included in the present invention.

The present invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^{3}H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent.

The term $C_{1-4}$ alkyl as used herein as a group or a part of the group refers to a straight or branched alkyl group containing from 1 to 4 carbon atoms; examples of such groups include methyl, ethyl, propyl, isopropyl, n-butyl, isobutyl or tert butyl.

The term $C_{2-6}$ alkenyl as used herein refers to a straight or branched alkenyl group containing from 2 to 6 carbon atoms examples of such groups include vinyl, propenyl, isoprope-nyl, n-butenyl, isobutenyl, pentenyl, hexenyl and the like.

The term $C_{1-4}$ alkoxy as used herein as a group or a part of the group refers to a straight or branched alkyl group containing from 1 to 4 carbon atoms attached to an oxigen atom; examples of such groups include methoxy, ethoxy, propoxy, isopropoxy, n-butoxy, isobutoxy or tert butoxy.

The term halogen refers to a fluorine, chlorine, bromine or iodine atom.

When R represents halogen this is suitably chlorine or more preferably fluorine or when R is $C_{1-4}$ alkyl this is suitably methyl.

When m is 2 or 3, each of the two or three groups R may be the same or different. Similarly, when n is 2 or 3, each of the two or three $R_1$ groups may be the same or different.

Suitable values for $R_1$ include trifluoromethyl or halogen.
Suitable values for $R_2$ and $R_3$ include hydrogen or methyl.
For compounds of formula(I) n is preferably 2.

A preferred class of compound of formula(I) are those wherein R is selected from trifluromethyl, methyl or halogen,(e.g fluorine), $R_1$ is trifluoromethyl or halogen, $R_3$ is methyl, $R_2$ is methyl or hydrogen and n is 2.

Preferred compounds according to the invention are:
(+/−)1-(4-Fluoro-2-methyl-phenyl)-piperazine-2-carboxylic acid, (3,5-bis-trifluoromethyl-benzyl)-methylamide;
(+/−)1-(4-Fluoro-2-methyl-phenyl)-piperazine-2-carboxylic acid (3,5-dichloro-benzyl)-methylamide;
(+/−)1-(4-Fluoro-2-methyl-phenyl)-piperazine-2-carboxylic acid [1-(3,5-dichloro-phenyl)-ethyl]-methylamide;
(+/−)1-(4-Fluoro-2-methyl-phenyl)-piperazine-2-carboxylic acid (3,5-dichloro-benzyl)-(±methylamide;
(+/−)1-(4-Fluoro-2-methyl-phenyl)-piperazine-2-carboxylic acid (3,5-bis-trifluoromethyl-benzyl)-methylamide;
(+/−)1-(4-Fluoro-2-methyl-phenyl)-piperazine-2-carboxylic acid (3,4-dibromo-benzyl)-methylamide;
(+/−)1-(4-Trifluoromethyl-phenyl)-piperazine-2-carboxylic acid (3,5-bis-trifluoromethyl-benzyl)-methylamide;
and enantiomers, diastereoisomers, pharmaceutically acceptable salts (e.g. hydrochloride) and solvates thereof.

Particular preferred compounds of the invention are
(+/−)1-(4-Fluoro-2-methyl-phenyl)-piperazine-2-carboxylic acid (3,5-dichloro-benzyl)-methylamide;
(+)1-(4-Fluoro-2-methyl-phenyl)-piperazine-2-carboxylic acid (3,5-dichloro-benzyl)-methylamide;
(−)1-(4-Fluoro-2-methyl-phenyl)-piperazine-2-carboxylic acid (3,5dichloro-benzyl)-methylamide;
and amorphous and crystalline forms thereof and pharmaceutically acceptable salts (e.g. hydrochloride) and solvates thereof.

The compounds of the invention are antagonists of tachykinin receptors, including substance P and other neurokinins, both in vitro and in vivo and are thus of use in the treatment of conditions mediated by tachykinins, including substance P and other neurokinins.

Tachykinins are a family of peptides that share a common carboxyl-terminal sequence (Phe-X-Gly-Leu-Met-NH2). They are actively involved in the physiology of both lower and advanced lifeforms. In mammalian lifeforms the main tachykinins are subtance P (SP), Neurokinin A (NKA) and Neurokinin B (NKB) which act as neurotransmitters and neuromodulators. Mammalian tachykinins may contribute to the pathophysiology of a number of human diseases.

Three types of tachykinins receptors have been identified, namely NK1(SP-preferring), NK2 (NKA-preferring) and NK3 (NKB-preferring) which are widely distributed throughout the central nervous (CNS) and peripheral nervous system.

Particularly the compounds of the invention are antagonists of the NK1 receptor.

The compounds of the present invention also have activity as selective serotonin reuptake inhibitors (hereinafter referred to as SSRIs) and are thus of use in the treatment of conditions mediated by selective inhibition of the serotonin reuptake transporter protein.

Thus the compounds of the present invention combine dual activity as tachykinin antagonists, including substance P and other neurokinins, and as SSRIs. In particular, the compounds of the invention combine dual activity as NK1 receptor antagonists and as SSRIs.

In those compounds of the invention which exhibit stereoisomererism, this dual NK1 and SSRIs activity may in certain cases be exhibited by isomeric mixtures, including racemic mixtures or by individual stereoisomers comprised in a stereoisomeric mixture.

In some cases the relative level of NK1 and SSRIs activity, in vitro or in vivo, may differ between individual stereoisomers of a stereisomeric mixture. In some other cases individual stereoisomers may exibit synergy when present in combination as a stereoisomeric mixture i.e the individual levels of NK1 and SSRIs activity of a stereisomeric mixture may be greater than the level of activity associated with individual stereoisomers comprised in the stereisomeric mixture.

Thus, in certain compounds of the invention, the enantiomers comprising a racemic mixture may exhibit synergy such that the levels of NK1 and SSRIs activity of the racemate are higher than the individual levels of NK1 and SSRIs activity of the individual enantiomers.

By virtue of their efficacy as tachykinins receptor (expecially NK1 receptor) antagonists and as SSRIs, the compounds of the present invention are particularly useful for the treatment of of CNS disorders and psychotic disorders, in particular in the treatment or prevention of depressive states and/or in the treatment of anxiety.

$NK_1$-receptor binding affinity has been determined in vitro by measuring the compounds' ability to displace [3H]-substance P (SP) from recombinant human $NK_1$ receptors expressed in Chinese Hamster Ovary (CHO) cell membranes.

CHO cell membranes were prepared by using a modification of the method described by Beattie D. T. et al. (Br. J. Pharmacol, 116:3149–3157, 1995). Briefly, ligand binding was performed in 0.2 ml of 50 mM HEPES, pH 7.4, containing 3 mM $MnCl_2$, 0.02% BSA, 0.5 nM [$^3$H]-Substance P (30÷56 Ci/mmol, Amersham), a final membrane concentration of 20÷30 μg of protein/ml, and the test compounds. The incubation proceeded at room temperature for 40 min and stopped by filtration. Non-specific binding was determined using excess of Substance P (1 μM) and represents about 6÷10% of the total binding.

Compounds of the invention were further characterised in a finctional assay for the determination of their effect to inhibit the intracellular calcium increase induced by SP in Human-$NK_1$-CHO cells using FLIPR technology. Briefly, after 30 min incubation with the cytoplasmic calcium indicator Fluo-4 AM (2 μM), cells were washed and incubated in the absence or presence of three different concentrations of antagonist for 60 min, at 37° C. in Hank's balanced salts with 20 mM Hepes, and then non-cumulative concentration-response curves of SP (2 pM-300 nM) was performed. The potency of the antagonist ($pK_B$ value) was calculated from Schild's analysis.

The action of the compounds of the invention at the $NK_1$ receptor and/or serotonin transporter may be determined by using conventional animal models. Thus the ability to bind at the $NK_1$ receptor and/or serotonin tmnsporter was determined using the guinea pig pup isolation calls model as described by Pettijohn, Psychol. Rep., 1979 and Rupniak et al., Neuropharmacology, 2000.

Human Serotonin Transporter (hSERT) binding affinity has been determined in vitro by the compounds' ability to displace [$^3$H]-Imipramine from human serotonin transporter expressed in Human Embryonic Kidney HEK293 cell membranes (Receptor Biology Inc.). For the binding reaction, 4 nM of [$^3$H]-Imipramine (703 GBq/mmol, Amersham) were incubated with 0.02 mg/ml of cell membrane and the compound to be tested at different concentrations (7 concentration points) in 50 mM Tris HCl, pH 7.5, 120 mM of NaCl and 5 mM KCl. The reaction was performed for 60 min at 4° C. and was terminated by through GF/B Unifilter (pre-soaked in 0.5% PEI) using a Cell Harvester (Packard). Scintillation fluid was added to each filtered spot and radioactivity was determined using a scintillation counter (TopCount (Packard)). Non-specific binding was determined using Imipramine (100 μM) and represents about 5% of the total binding.

For the preferred compounds of the invention Human Serotonin Transporter binding affinity has been also determined in vitro by the compounds ability to displace [3H] paroxetine.

Competition experiments were conducted with duplicate determination for each point.

Msat601 software package was used to elaborate the competition binding data.

$IC_{50}$ values were converted to $K_i$ values using Cheng-Prusoff equation.

The inhibitory activity of the compounds at the rat serotonin transporter has been determined in vitro using rSERT-LLCPK cells (LLCPK cells tranfected with the rat SERT). The cells have been plated onto 96-well plates (60000 cells/well). After 24 hr, cells have been washed in uptake buffer (Hank's balanced salt solution+20 mM Hepes) and pre-incubated for 10 min at RT with 50 μl of buffer containing the test compounds. 50 μl of 50 nM [3H] Serotonin (5HT) solution (final concentration: 25 nM [3H] 5HT) have been added and plates have been incubated for 7 min at RT, during which cells take up radiolabelled 5HT. Aspirating the solution and rapidly washing the cells with cold buffer has terminated the uptake.

The amount of radioactive 5HT incorporated in the cells has been then measured by adding the scintillation cocktail directly onto the cells and reading the plate in the Top Count. The data have been digitally processed to obtain the pIC50 values of the antagonists. The pKi values have been calculated using the Chen-Prusoff equation.

Compounds of the invention are useful in the treatment of CNS disorders and psychotic disorders, in particular in the treatment or prevention of depressive states and/or in the treatment of anxiety as defined in, but not restricted to, Diagnostic Statistical of mental disorder (DSM) IV edition edit by American Psychiatric association and international classification Diseases 10th revision (ICD10).

Thus for example depressive states include Major Depressive Disorder (MDD), including bipolar depression, unipolar depression, single or recurrent major depressive episodes, recurrent brief depression, with or without psychotic features, catatonic features, melancholic features including anorexia, weight loss, atypical features, anxious depression, cyclothymic or postpartum onset.

Other mood disorders encompassed within the term major depressive disorders include dysthymic disorder with early or late onset and with or without atypical features, neurotic depression, post traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

The term anxiety includes anxiety disorders, such as panic disorders with or without agoraphobia, agoraphobia, phobias for example social phobias or agoraphobia, obsessive-compulsive disorder, stress disorders including post traumatic stress disorder generalised anxiety disorder, acute stress disorders and mixed anxiety-depression disorders.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful in the treatment of sleep disorders including dysomnia, insomnia, sleep apnea, narcolepsy, and circadian ritmic disorders.

Compounds of the invention are also useful in the treatment or prevention of the cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment or prevention of schizophrenic disorders including paranoid schizophrenia, disorganised schizophrenia, catatonic schizophrenia, undifferentiated schizophrenia, residual schizophrenia.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g, cyclophospharide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer, poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercrnnial pressure (e.g. altitude sickness); opioid analgesics, such as morphine; and gastro-oesophageal reflux disease, acid indigestion, overindulgence of food or drink acid stornach, sour stomach, waterbrash/regurgitation, heartburn, such as episodic heartburn, nocturnal heartburn, and meal-induced heartburn and dyspepsia.

Compounds of the invention are also useful in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

The compounds of the invention are also useful in premenstrual dysphoric disorder PMDD), in chronic fatigue syndrome and Multiple sclerosis.

Compounds of the invention have been found to exhibit anxiolytic and antidepressant activity in conventional tests. For example in Guinea pig pups separation-induced vocalisations (Molewijk et al., 1996).

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins (including substance P and other neurokinins) and/or by selective inhibition of serotonin reuptake.

There is also provided as a further aspect of the invention the use of a compound of formula (I) or a pharmaceutically acceptable salt or solvate thereof in the treatment of conditions mediated by tachykinins (including substance P and other neurokinins) and/or by selective inhibition of the serotonin reuptake transporter protein.

In a further aspect there is provided the use of a compounds of formula(I) or a pharmaceutically acceptable salt or solvate thereof in the preparation of a medicament for use in the treatment of depression and /or anxiety.

In an alternative or further aspect there is provided a method for the treatment of a mammal, including man, in particular in the treatment of conditions mediated by tachykinins, including substance P and other neurokinins and/or by selective inhibition of the serotonin reuptake transporter protein comprising administration of an effective amount of a compound of formula (I) or a pharmaceutically acceptable salt thereof.

In a further aspect of the present invention is provided a method for the treatment of a manmal, including man, in particular in the treatment of depression and/or anxiety which method comprises administration of an effective amount of a compound of formula (I) or a pharmaceutically acceptable salt or solvate thereof.

It will be appreciated that reference to treatment is intended to include prophylaxis as well as the alleviation of established symptoms.

Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt or a solvate thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Thus for parenteral administration a daily dose will typically be in the range of 1 to about 100 mg, preferably 1 to 80 mg per day. For oral administration a daily dose will typically be within the range 1 to 300 mg e.g. 1 to 100 mg.

Compounds of formula (I), and salts and solvates thereof, may be prepared by the general methods outlined hereinafter. In the following description, the groups R, $R_1$, $R_2$, $R_3$, m and n have the meaning as previously defined for compounds of formula (I) unless otherwise stated.

A compound of formula (I) may be prepared by reaction of an activated derivative of the carboxylic acid of formula (II), wherein $R_a$ is a suitable nitrogen protecting group, with amine (III) or salts thereof, optionally in the presence of a suitable base, followed by removal of the protecting group $R_a$,

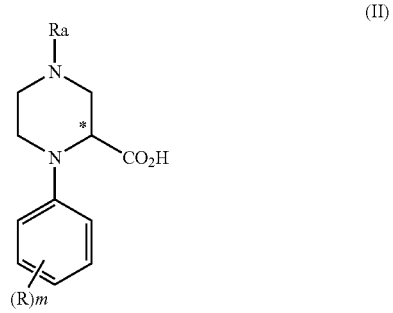

(II)

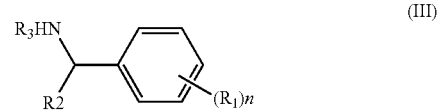

(III)

Suitable activated derivatives of the carboxyl group include the corresponding acyl halide, mixed anhydride, activated ester such as a thioester or a derivative formed between the carboxylic acid group and a coupling agent such as that used in peptide chemistry, for example O-(benzotriazol-1-yl)-N,N,N'N'-tetramethyluronium tetrafluoroborate.

The reaction is preferably carried out in an aprotic solvent such as an ether, e.g. tetrahydrofuran, a halohydrocarbon, e.g. dichloromethane, N,N-dimethylformamide or acetonitrile.

Suitable base for use in this reaction include organic base such as triethylamine or N,N diisopropylethylamine.

The activated derivatives of the carboxylic acid (II) may be prepared by conventional means. A particularly suitable activated derivative for use in this reaction is obatained by reaction of the carboxylic acid (II) with O-(benzotriazol-1-yl)-N,N,N'N'-tetramethyluronium tetrafluoroborate in a suitable aprotic solvent such as an ether e.g. tetrahydrofuran, a halohydrocarbon e.g. dichloromethane, an amide e.g. N,N-dimethylformamide or acetonitrile.

Compounds of formula (II) may be prepared by treating compounds of formula (IV) wherein $R_a$ has the meaning defined in formula (II), with a compound of formula (V),

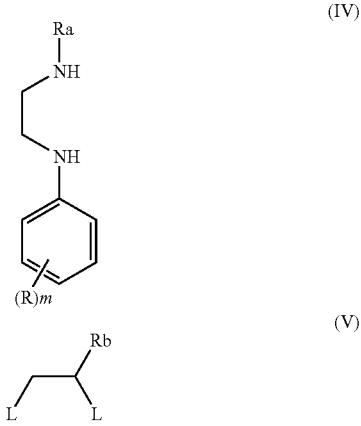

wherein L is a suitable leaving group such as halogen (e.g. chlorine, bromine or iodine) and Rb is an appropriate group capable to be converted into the carboxylic group, followed by conversion of Rb into the carboxylic group.

Suitable Rb groups for use in this reaction include a carboxyl protected group or a cyano group.

The reaction conveniently takes place in an aprotic solvent such as a hydrocarbon (e.g. toluene) optionally in the presence of a base such as a tertiary amine (e.g. diisopropylethylamine) and preferably with heating e.g. 40°–120° C.

When Rb is a carboxyl protected group, example of suitable groups includes allyloxycarbonyl, alkyloxycarbonyl (e.g. methoxycarbonyl, ethoxycarbonyl, t-butyloxycarbonyl) arylmethyloxycarbonyl (e.g. benzyloxycarbonyl or p-nitrobenzyloxycarbonyl) and the like.

When Rb is a carboxyl protected group, the conversion into carboxylic acid may be carried out using known procedure for removing carboxylic protecting groups.

Thus when Rb is methoxycarbonyl or ethoxycarbonyl the conversion into carboxylic group may be carried out by alkaline hydrolysis using, for example, sodium hydroxide or lithium hydroxide in a suitable solvent such as tetrahydrofuran or an alkanol e.g. methanol or isopropanol.

When Rb is a cyano group, the conversion into the carboxylic group may be carried out by reduction of the cyano group with lithium aluminum hydride.

Compounds of formula (IV) may be prepared by reduction of an amide compound of formula (VI)

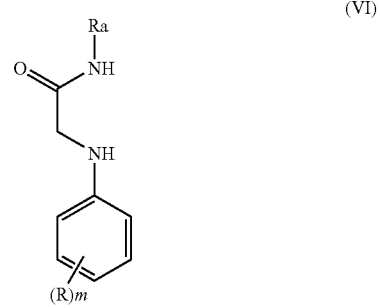

An appropriate reducing agent for this reaction includes for example borane or a borohydride, e.g. sodium borohydride, sodium borohydride, sodium cyanoborohydride or triacetoxy borohydride.

The reaction conveniently takes place in a suitable solvent such as alcohol (i.e. ethanol or methanol) at a temperature ranging between room temperature and reflux temperature.

A compound of formula (VI) may be prepared by alkylation of a compound of formula (VII), wherein $R_a$ represents a nitrogen protecting group and L is a leaving group as defined above, with amine (VIII).

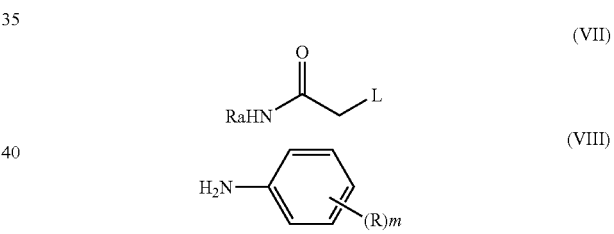

The reaction may be carried out in an aprotic solvent such as dichloromethane or alkyl esters (e.g. ethylacetate) and in the presence of an organic base such as triethylamine.

When $R_a$ is a nitrogen protecting group, examples of suitable groups include alkoxycarbonyl e.g. t-butoxycarbonyl, benzyloxycarbonyl, arylsulphonyl e.g. phenylsulphonyl, arylmethyl e.g benzyl or 2-trimethylsilylethoxymethyl.

Protection and deprotection may be effected using conventional techniques such as those described in "Protective Groups in Organic Synthesis $2^{nd}$ Ed." by T. W. Greene and P. G. M. Wuts (John Wiley and Sons, 1991) and as described in the examples hereinafter.

Thus when $R_a$ is a benzyl group, this may be removed by hydrogenation in a suitable solvent such as ethanol or methanol or by hydrolysis in the presence of haloformiates such as for example chloroformiates and in the presence of a suitable organic base.

In a preferred embodiment of the invention compound of formula (IV) may be prepared by reaction of a compound of formula(IX), wherein L is a suitable leaving group such as halogen (i.e chlorine or bromine) or mesilate, with $NH_2Ra$ wherein Ra is a suitable nitrogen protecting group.

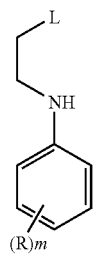

(IX)

The reaction conveniently takes place in an aprotic solvent such as an aprotic solvent optionally in the presence of a base such as a tertiary amine and preferably with heating e.g. 40°–120° C.

Compounds of formula (VII) and (VIII) are commercially available.

Compounds of formula (IX) may be prepared by analogous methods to those used for known compounds.

Thus for example compounds of formula (IX) may be prepared according to the preparation described in Tulyaganov, S. R. and Khasanov, S. A, Uzb. Khim. Zh. (1971), 15(2), 62–4) or Sineokov, A. et al., Zh. Org. Khim. (1968), 4(2), 284–7.

The compounds of formula (I) may be readily isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, specific enantiomers of the compounds of formula (I) may be prepared by reaction of a suitable chiral alcohol, in the presence of a source of a carbonyl group (such as triphosgene or carbonyl diimidazole) separating the resulting diastereoisomeric carbamates by conventional means, e.g. chromatography or by fractional crystallisation. The required enantiomer of a compound of general formula (I) may be isolated by removal of carbamate and conversion into the required free base or salts thereof.

Suitable chiral alcohols for use in the process include (R)-sec-phenylethyl alcohol.

Alternatively, the required enantiomer may be obtained from racemic compounds of formula (I) by use of chiaral HPLC procedures.

Alternatively, enantiomers of a compound of general formula (I) may be synthesised from the appropriate optically active intermediates using any of the general processes described herein. Thus, for example, the required enantiomer may be prepared by the corresponding enantiomeric acid of formula (II) using any of the process described above for preparing compounds of formula (I) from the acid (II).

The single enantiomer of acid (III) may be prepared from the racemic acid (III) using conventional procedures such as salt formation with a suitable optically active amine, such as (R)-α-phenylethylamine, (S)-α-phenylethylamine, brucine, cinconidine, quinine, followed by separation of the two diasteroisomer salts obtained and regeneration of the free acid. The two diastereoisomer salts may be conveniently separated by conventional means such as fractionally crystallisation or by chromatography.

In a further embodiment of the invention the specific enantiomer of acid (II) may by prepared by esterification of racemic acid (II) with a suitable optically active alchool, separating the resulting diastereoisomeric esters by conventional means e.g. chromatography, followed by hydrolysis of the required single diastereomeric ester.

Suitable chirals alcohols for use in this process include S(+)-indanol, S(+)methylmandelate, S(-) methyl lactate or R(+) t-butyl lactate.

The diastereoisomeric esters of a compound of formula (II) may be prepared by conventional means such as reaction of the chiral alcohol with an activated derivative of a compound of formula (II) in an aprotic solvent such as ether e.g. tetrahydrofuran.

The activated derivative of a compound of formula (II) may be prepared from a compound of formula (II) using conventional means for preparing activated derivatives of a carboxylic acid groups such as those conveniently used in peptide synthesis.

A convenient method of preparing the diastereoisomeric esters of a compound of formula (II) is to prepare the activated derivative of a compound of formula (II) in the presence of the chiral alcohol.

Thus, for example, a compound of formula (II) may be treated with the Mitsunobu combination of reagents, i.e. a dialkylazo-dicarboxylate such as diethylazodicarboxylate and a triarylphosphine e.g. triphenylphosphine in the presence of the chiral alcohol.

The reaction conveniently takes place in the presence of a suitable solvent such as an ether (e.g. diethylether or tetrahydrofiran), a halohydrocarbon (e.g. diethylether or tetrahydrofuran), a halohydrocarbon (e.g. dichloromethane) or a nitrile (e.g. acetonitrile) or a mixture thereof, at a temperature ranging from 0–30° C.

The required single diastereoisomeric ester of a compound of formula (I) substantially free of the other diastereoisomers may be obtained from the mixture thereof by conventional means, for example by the use of conventional chromatographic procedures such as preparative HPLC or by fractional crystallization.

The required enantiomer may be prepared from the corresponding single diastereoisomeric ester of a compound of formula (I) by hydrolysis, e.g. alkaline hydrolysis. Thus, for example, the hydrolysis may be carried using an alkali metal hydroxide e.g. sodium hydroxide or lithium hydroxide in a solvent such as an ether, e.g. tetrahydrofuran, and water.

Physiologically acceptable salts of compounds of formula (I) may be prepared by treating the corresponding base with an appropriate acid in a suitable solvent.

The invention is further illustrated by the following Intermediates and Examples which are not intended as a limitation of the invention.

Pharmaceutically acceptable salts may also be prepared from other salts, including other pharmaceutically acceptable salts, of the compound of formula (I) using conventional methods In the Intermediates and Examples unless otherwise stated:

Melting points (m.p.) were determined on a Gallenkamp m.p. apparatus or a Büchi 530 melting point apparatus and are uncorrected. All temperatures refers to ° C. Infrared spectra were measured on a FT-IR instrument. $^1$H-NMR spectra were recorded at 400 or 500 MHz, chemical shifts are reported in ppm (δ) using the residual solvent line as internal standard. The signals are assigned as singlets (s), doublets (d), doublets of doublets (dd), triplets (t), quartets (q) or multiplets (m). Flash column chromatography was carried out over silica gel (Merck AG Darmstaadt, Germany). SFC (Supercritical Fluid Chromatography was performed on a Diacel chiral pack AD column (25×0.46 cm i.d., 5 μm) using the following conditions: column oven temperature 35° C., mobile phase carbon dioxide +35% EtOH (with 0.1% vv isopropylamine), flow 2.5 mL/min, UV detection at 225 nm.

The following abbreviations are used in the text: AcOEt=ethyl acetate, CH=cyclohexane, DCM=dichloromethane, EtOH=ethanol, Et2O=diethyl ether, DIPEA=N,N-diisopropylethylamine, DMF=N,N'-dimethylformamide, MeOH=methanol, TEA=triethylamine, TFA=trifluoroacetic acid, THF=tetrahydrofuran. Tlc refers to thin layer chromatography on silica plates, and dried refers to solution dried over anhydrous sodium sulphate; r.t. (RT) refers to room temperature.

Enantiomer 1, enantiomer 2, diastereoisomer 1 or diastereoisoiner 2 refer to a single enantiomer or a single diasteroisomer respectively, whose absolute stereochemistry was not characterised.

Diastereoisomer A or diastereoisomer B refer to a mixture of two diastereoisomers whose absolute stereochemistry was not characterised.

The X-ray powder diffraction pattern of a crystalline form of the compounds of the invention was obtained by loading the sample into the diffractometer (Siemens D5005 X-ray diffractometer equipped with θ/θ goniometer, scintillation counter and graphite monochromator. The diffractometer was set up with the instrumental parameters given below:

Instrumental Parameters

MONOCHROMANIC RADIATION: Cu-1.54056/1.54439
2θ RANGE: 2°-45° 2θ
GENERATOR VOLTAGE/CURRENT: 40 kV/50 mA
STEP SIZE: 0.02° 2θ
TIME PER STEP: 10 sec
ROTATION: on
DIVERGENCE/ANTISCATTERING SLIT: variable
SAMPLE HOLDER: on zero-background plate.

The spectrum obtained was analysed using the data evaluation software EVA3.0.

Intermediate 1

N-Benzyl-2-(4-fluoro-2-methyl-phenylamino)acetamide

A solution of chloroacetyl chloride (11.4 mL) was added drop-wise over 1 hour to a stirred solution of benzylamine (15 mL) and TEA (23 mL) in dry TFP (200 mL) previously cooled at 0–3° C. under a Nitrogen atmosphere. The dark suspension was allowed to warm gradually to r.t. and then stirred at r.t. for 3 hours. The inorganic salts were filtered and washed with AcOEt (300 mL). The filtrate was washed with 2N hydrochloric acid solution (2×250 mL), sodium hydrogen carbonate (2×200 mL) and water (200 mL). The organic layer was dried and concentrated in vacuo to give a dark solid, which was crystallized from Et₂O/CH (1:1, 700 mL) to give N-benzyl-2-chloroacetamide (17.8 g) as a grey solid (T.l.c.: AcOEt 100%, Rf=0.47).

A mixture of N-benzyl-2-chloroacetamide (17.8 g), DIPEA (19.5 mL) and 4-fluoro-2-methyl-aniline (10.6 mL) in anhydrous DMF (174 mL) was stirred at 100° C. for 40 hours under a Nitrogen atmosphere. After cooling to r.t., the dark solution was partitioned between AcOEt (200 mL) and water (200 mL). The separated aqueous phase was extracted with further AcOEt (3×200 mL). The combined organic extracts were washed with water (200 mL), dried and concentrated in vacuo. The residue was purified by flash chromatography (CH/AcOEt 2:8) to give a dark solid, which was triturated with CH to give the title compound as a beige solid (16.2 g).

T.l.c.: AcOEt/CH 8:2, Rf=0.48. M.p.: 75–76° C. IR (nujol, cm⁻¹): 3395 and 3294 (NH), 1642 (C=O). ¹H-NMR (d₆-DMSO): δ (ppm) 8.39 (t, 1H); 7.26 (t, 2H); 7.19 (t, 1H); 7.18 (d, 2H); 6.87 (dd, 1H); 6.81 (td, 1H); 6.28 (dd, 1H); 5.25 (t, 1H); 4.27 (d, 2H); 3.7 (d, 2H); 2.12 (s, 3H). MS (AB/NBA): m/z=272 [M]⁺.

Intermediate 2

N-Benzyl-N'-(4-fluoro-2-methyl-phenyl)-1,2-ethylenediamine

Method A

Borane (1M solution in THF, 30.4 mL) was added drop-wise at r.t. to a solution of intermediate 1 (1 g) in dry TBF (100 mL) under a Nitrogen atmosphere. The mixture was heated to reflux for 24 hours, then it was cooled to r.t., poured into conc. hydrochloric acid and extracted with AcOEt. The organic phase was concentrated in vacuo, was diluted in DCM and washed with a solution of potassium hydroxide until the aqueous phase has pH=7. The organic phase was dried and concentrated in vacuo to give the title compound (0.86 g) as a whitish wax.

T.l.c.: AcOEt 100%, Rf=0.14. ¹H-NMR (d₆-DMSO): δ (ppm) 7.33 (m, 5H); 6.82 (m, 2H); 6.48 (dd, 1H; 4.68 (bt, 1H); 3.76 (s, 2H); 3.13 (bm, 211); 2.76 (t, 2H); 2.07 (s, 3H). MS (ES/+): m/z=259 [M]⁺.

Method B

TEA (1.86 mL) was added over 15 minutes to a solution of intermediate 60 (1 g) is suspended in AcOEt (8 mL) at 20° C. The resulting mixture was cooled to 5° C. and methanesulfonyl chloride (0.61 g) was added in 30 minutes keeping the internal temperature under 10° C. Once finished the addition the mixture was heated to 15° C. The organic mixture was washed with a saturated ammonium chloride solution (3×4 mL) and with water (4 mL). The solution was concentrated to 4 mL and AcOEt (4 mL) was added. Finally it was concentrated again to 4 mL and benzylamine (2.08 g) was added. The mixture was heated to 50° C. for 1 hour then AcOEt (4 mL) was added and the resulting solution was heated at 78° C. for 15–20 hours.

The following day the mixture was cooled to 20° C. and washed with a 13% ammonium chloride solution (5×5 mL) and H2O (5 mL). The organic was concentrated to 4 mL and AcOEt (5 mL) is added. Under suitring at 20° C. hydrochloric acid (5–6N in isopropanol—1.25 mL) was dropped. The precipitate was then stirred for 2 hours. The solid was filtered and washed with AcOEt (3 mL)and then dried for 18 hours at 40° C. to obtain the title compound.(1.19 g)

¹H-NMR (d₆-DMSO): δ (ppm) 9.74 (bs, 2H); 7.62 (m, 2H); 7.41 (m, 3H);6.92 (dd, 1H); 6.88 (dt, 1H); 6.72 (bm, 1H); 4.17 (bs, 2H); 3.50 (t, 2H); 3.13 (bm, 2H); 2.18 (s, 3H).

Intermediate 3

4-Benzyl-1-(4-fluoro-2-methyl-phenyl)-piperazine-2-carboxylic acid ethyl ester

A solution of intermediate 2 (3.3 g) and DIPEA (7.3 mL) in toluene (40 mL) was added to a solution of ethyl 2,3-dibromopropionate (3.7 mL) in toluene (70 mL) previously heated at 50° C. under a Nitrogen atmosphere. The mixture was then stirred at 100°–105° C. for 19 hours. The mixture was cooled to r.t., then diluted with AcOEt (150 mL) and toluene (50 mL) and washed with water (150 mL). The separated organic phase was concentrated in vacuo and the residue was purified by flash chromatography (CH/AcOEt 9:1) to give the title compound (1.3 g) as a yellow oil.

T.l.c.: CH/AcOEt 9:1, Rf=0.44. IR (film, cm$^{-1}$): 1741 (C=O), 1497 (C=C). $^1$H-NMR (d$_6$-DMSO): δ (ppm) 7.2–7.35 (m, 5H); 7.16 (dd, 1H); 6.95 (dd, 1H); 6.9 (td, 1H); 3.84 (m, 1H); 3.8–3.4 (m, 2H); 3.6 (d, 1H); 3.47 (bm, 1H); 3.41 (d, 1H); 2.79 (m, 1H); 2.71 (m, 1H); 2.64 (m, 1H); 2.57 (bd, 1H); 2.43 (bt, 1H); 2.21 (s, 3H); 0.97 (t, 3H). MS (ES/+): m/z=357 [M+H]$^+$.

Intermediate 4

4-Benzyl-1-(4-fluoro-2-methyl-phenyl)-piperazine-2-carboxylic acid

A solution of intermediate 3 (1.3 g) in MeOH (42 mL) containing 1M aqueous lithium hydroxide solution (7.2 mL) was stirred at 70° C. for 20 hours. The solution was allowed to cool to r.t., neutralized with 1N hydrochloric acid and concentrated in vacuo. The residue was diluted with AcOEt (30 mL) and washed with water (25 mL). The aqueous phase was further extracted with AcOEt (2×10 mL). The combined organic extracts were dried and concentrated in vacuo to give the title compound (1.2 g) as a white foam.

T.l.c.: CH/AcOEt 8:2, Rf=0.16. IR (film, cm$^{-1}$): 3397 (NH), 1733 (C=O). $^1$H-NMR (d$_6$-DMSO): δ (ppm) 12.4 (bs, 1H); 7.37 (m, 5H); 7.12 (dd, 1H); 6.97 (dd, 2H); 4.0–3.7 (mn, 2H); 3.5–2.5 (m, 6H); 2.25 (s, 3H). MS (ES/+): m/z=329 [M+H]$^+$.

Intermediate 4a

4-Benzyl-1-(4-fluoro-2-methyl-phenyl)-piperazine-2-carboxylic acid hydrochloride Intermediate 3 (1 g) was suspended in MeOH (6 mL), isopropanol (2 mL) and a 1M sodium hydroxide solution (8 mL). The reaction mixture was heated to 75–78° C. over 4–5 hours. Then the mixture was cooled to 50° C. and concentrated to 9 mL. The mixture was cooled to 25° C. then AcOEt (15 mL) was added and a 10% hydrochoric acid solution (3 mL) was dropped over 10 minutes.

The two phases were separated and the aqueous one was extracted with further AcOEt (10 mL). The combined organic extracts were concentrated to 4 mL then AcOEt (8 mL) was added and concentrated to 4 mL. Finally AcOEt (8 mL) was added and concentrated again to 4 mL.

AcOEt (3.5 mL) was added and if no precipitated was observed a seed was added. Then methyl-tert-butyl-ether (2.5 mL) was dropped to increase precipitation and the obtained solid was stirred overnight at room temperature. It was then filtered and washed with AcOEt/methyl-tert-butyl-ether 1/1 (2 mL).

After drying at 40° C. in a vacuum oven (12 hours) the title compound (0.8 g) was obtained as a white solid.

$^1$H-NMR (d$_6$-DMSO): δ (ppm) 13.0–11.9(2bs, 2H); 7.66 (bs, 2H); 7.47 (m, 3H);7.12 (m, 1H); 6.99 (m, 2H); 4.46–4.36 (bd, 2H); 4.3 (b, 1H); 3.8–2.9 (bm, 6H); 2.27 (bs, 3H).

Intermediate 5

4-Benzyl-1-(4-fluoro-2-methyl-phenyl)-piperazine-2-carboxylic acid (3,5-bis-trifluoromethyl-benzyl)-methylamide DIPEA (1.6 mL) and O-(benzotriazol-1-yl)-N,N,N'N'-tetramethyluronium tetrafluoroborate (1.2 g) were added to a solution of intermediate 4 (1 g) in anhydrous DMF (50 mL) under a Nitrogen atmosphere. After stirring for 5 minutes, 3,5-bis(trifluoromethyl)-benzyl-methylamine hydrochloride (0.94 g) was added and the mixture was stirred at r.t. for 16 hours. The orange solution was partitioned between AcOEt (150 mL) and water (150 mL). The separated aqueous phase was further extracted with AcOEt (2×100 mL). The combined organic extracts were washed with water (3×100 mL), dried and concentrated in vacuo to a residue which was purified by flash chromatography (CH/AcOEt 1:1) to give the title compound (1.4 g) as yellow oil.

T.l.c.: AcOEt/CH 6:4, Rf=0.57. IR (film, cm$^{-1}$): 1652 (C=O). $^1$H-NMR (d$_6$-DMSO): δ (ppm) 7.88 (s, 1H); 7.55 (s, 2H); 7.4–7.2 (m, 4H); 7.0 (m, 1H); 7.14 (d, 1H); 6.8–6.75 (m 2H); 4.6 (m, 1H); 4.4 (m, 2H); 3.59 (s, 2H); 3.02 (s, 3H); 3.0–2.3 (m, 6H); 2.2 (s, 3H). MS (ES/+): m/z=568 [M+H]$^+$.

Intermediate 6

1-(4-Fluoro-2-methyl-phenyl)-piperazine-2-carboxylic acid ethyl ester

A mixture of the intermediate 3 (1.0 g) in EtOH (100 mL) containing glacial acetic acid (1 mL) and 10% palladium on carbon (400 mg) was stirred under hydrogen at 5 atm. for 19 hours. The mixture was filtered through a pad of celite, and the filtrate was concentrated in vacuo. The residue was dissolved in AcOEt and the solution was washed with a saturated sodium carbonate solution. The organic layer was dried and concentrated in vacuo to give the title compound (910 mg) as a yellow oil.

T.l.c.: AcOEt/MeOH 8:2, Rf=25. IR (CDCl$_3$, cm$^{-1}$): 1730 (C=O). $^1$H-NMR (CDCl$_3$): δ (ppm) 7.11 (m, 1H); 6.9–6.8 (m, 2H); 4.02 (m, 2H); 3.71 (t, 1H); 3.43 (m, 1H); 3.24 (m, 2H); 3.1–2.98 (m, 2H); 2.66 (m, 1H); 2.31 (s, 3H); 1.1 (t, 3H). MS (ES/+): m/z=267 [M+H]$^+$.

Intermediate 7

4-(4-Fluoro-2-methyl-phenyl)-piperazine-1,3-dicarboxylic acid 1-tert-butyl ester 3-ethyl ester Di-tert-butyl-dicarbonate (821 mg) and TEA (1.2 mL) were added to a solution of intermediate 6 (910 mg) in anhydrous DCM (50 mL) under a Nitrogen atmosphere. The solution was stirred at r.t. for 4 hours, then concentrated in vacuo. The residue was purified by flash chromatography (CH/AcOEt 8:2) to give the title compound (1.2 g) as a yellow oil.

T.l.c.: CH/AcOEt 1:1, Rf=0.64. IR (CDCl$_3$, cm$^{-1}$): 1732 and 1689 (C=O). $^1$H-NMR (CDCl$_3$): δ (ppm) 7.14 (dd, 1H); 6.9–6.8 (m, 2H); 4.05 (m, 2H); 3.95 (m, 1H); 3.73 (m, 3H); 3.45 (m, 2H); 2.7 (m, 1H); 2.31 (s, 3H); 1.48 (s, 9H); 1.12 (t, 3H). MS (ES/+): m/z=367 [M+H]$^+$, 389 [M+Na]$^+$.

Intermediate 8

4(4-Fluoro-2-methyl-phenyl)-piperazine-1,3-dicarboxylic acid 1-tert-butyl ester)

A solution of lithium hydroxide hydrate (0.63 g) in water (5 mL) was added to a solution of intermediate 7 (1.2 g) in MeOH (40 mL). The mixture was heated to 70° C. for 4 hours. The solution was allowed to cool to r.t, neutralised with 1N hydrochloric acid solution until pH=5 and extracted with DCM. The organic layer was dried, concentrated in vacuo and the residue was purified by flash chromatography (CH/AcOEt from 7:3 to 3:7) to give the title compound (770 mg) as pale yellow solid.

T.l.c.: CH/AcOEt 1:1, Rf=0.23. $^1$H-NMR (d$_6$-DMSO): δ (ppm) 13.0–12.0 (bm, 1H); 7.13 (m, 1H); 6.92 (m, 1H); 6.86 (m, 1H); 3.7 (m, 1H); 3.7–3.65 (m, 2H); 3.55 (m, 1H); 3.39–3.25 (m, 2H); 2.55 (m 1H); 2.26 (s, 3H); 1.41 (s, 9H). MS (ES/+): m/z=339 [M+H]$^+$.

Intermediates 8a and 8b

3-[1-(3,5-Dichloro-phenyl)ethyl]-methylcarbamoyl]-4-(4-fluoro-2-methyl-phenyl)-piperazine-1-carboxylic acid tert-butyl ester (8a-diastereoisomer A)

3-[1-(3,5-Dichloro-phenyl)-ethyl]-methylcarbamoyl]-4-(4-fluoro-2-methyl-phenyl)-piperazine-1-carboxylic acid tert-butyl ester (8b-diastereoisomer B)

DIPEA (127 μL) and O-(benzotriazol-1-yl)-N,N,N'N'-tetramethyluronium tetrafluoroborate (98.7 mg) were added to a solution of intermediate 8 (80 mg) in anhydrous DMF (4 mL) under a Nitrogen atmosphere. After stirring for 5 minutes, intermediate 62 (35 mg) was added and the mixture was stirred at r.t. for 18 hours. The solution was diluted with water (10 mL) and extracted with AcOEt (2×20 mL). The combined organic extracts were washed with brine (10 mL), dried and concentrated in vacuo. The residue was purified twice by flash chromatography (CH/AcOEt 9:1 the first time, then toluene/AcOEt 95:5) to give the title compound as:
diastereoisomer A (33 mg—T.l.c.: CH/AcOEt 6:4, Rf=0.6)
diastereoisomer B (28 mg—T.l.c.: CH/AcOEt 6:4, Rf=0.56).

Intermediate 9

3-[(3,5-Dichloro-benzyl)-methylcarbamoyl]-4-(4-fluoro-2-methyl-phenyl)-piperazine-1-carboxylic acid tert-butyl ester DIPEA (8 μL) and O-(benzotriazol-1-yl)-N,N,N'N'-tetramethyluronium tetrafluoroborate (60 mg) were added to a solution of intermediate 8 (50 mg) in anhydrous DMF (5 mL) under a Nitrogen atmosphere. After stirring for 5 minutes, 3,5-dichloro-benzyl-methylamine hydrochloride (35 mg) was added and the mixture was stirred at r.t. for 16 hours. The solution was partitioned between AcOEt (15 mL) and water (15 mL). The separated aqueous phase was further extracted with AcOEt (2×10 mL). The combined organic extracts were washed with water (3×100 mL), dried and concentrated in vacuo to a residue which was purified by flash chromatography (CH/AcOEt from 9:1 to 8:2) to give the title compound (65 g) as yellow oil.
T.l.c.: AcOEt/CH 6:4, Rf=0.61. MS (ES/+): m/z=510 [M+H]$^+$. $^1$H-NMR (d$_6$-DMSO—90° C.): δ (ppm) 7.37 (bs, 1H); 7.16 (m, 1H); 6.93 (m, 1H); 6.92 (bs, 2H); 6.83 (m, 1H); 4.59 (d, 1H); 4.1 (bd, 1H); 4.3–3.2 (bm, 6H); 2.96 (bs, 3H); 2.57 (m, 1H); 2.29 (bs, 3H); 1.43 (s, 9H).

Intermediate 9a

4-Benzyl-1-(4-fluoro-2-methyl-phenyl)-piperazine-2-carboxylic acid (3,5-dichloro-benzyl)-methylamide To a suspension of intermediate 4a (1 g) in DMF (3 mL) a solution of DIPEA (2.15 mL) was added. The mixture was stirred at room temperature over 10 minutes before the addition of O-benzotriazol-1-yl-N,N,N',N'-tetramethyluronium tetrafluoroborate (TBTU) (1.05 g). The reaction was stirred over 10 minutes then 3.5 dichloro-benzyl methylamine hydrochloride (0.64 g) was added. The so obtained solution was maintained at room temperature for 2 hours. The solution was diluted with AcOEt (6 mL) and water (6 mL). The two phases were separated and the organic layer was washed with additional water (3×6 mL).
The organic phase was diluted with AcOEt (6 mL) and concentrated to 6 mL. This operation was repeated again to remove the water to obtain the title compound (1.3 g)
$^1$H-NMR (d$_4$-DMSO): δ (ppm) 7.29 (m, 5H); 7.06 (dd, 1H); 7.00 (m, 1H);6.93 (m, 1H); 4.5–4.45 (2d, 2H); 3.8 (d, 1H); 3.7 (m, 1H); 3.42 (bd, 1H); 3.25 (b, 1H); 3.04 (bs,3H); 2.96 (m, 2H); 2.78 (m, 2H); 2.41 (b, 1H); 2.20 (s, 3H).

Intermediate 10

4-Benzyl-1-(4-fluoro-2-methyl-phenyl)-piperazine-2-carboxylic acid 1-(S)-tert-butoxycarbonyl-ethyl ester A solution of diethylazodicarboxylate (1.19 g) in anhydrous TBF (20 mL) was slowly dropped into a solution of intermediate 4 (1.13 g), triphenylphosphine (1.8 g) and R-(+)-tert-butyl lactate (0.95 g) in anhydrous THF (40 mL) under a Nitrogen atmosphere. The solution was stirred at r.t. for 24 hours, then further triphenylphosphine (0.9 g) was added followed by a solution of diethyl azodicarboxylate (0.5 mL) in anhydrous THF (5 mL). The solution was stirred for further 2 hours, then it was concentrated in vacuo. The residue was purified by flash chromatography (CH/Et2O 9:1) to give:
343 mg diastereoisomer 1 (intermediate 10a)
324 mg of diastereoisomer 2 (intermediate 10b)

Intermediate 10a

4-Benzyl-1-(4-fluoro-2-methyl-phenyl)-piperazine-2-carboxylic acid, 1-(S)-tert-butoxycarbonyl-ethyl ester (diastereoisomer 1)

T.l.c.: CH/Et2O 8:2, Rf=0.38. IR (film, cm$^{-1}$): 1745 (C=O). $^1$H-NMR (d$_6$-DMSO): δ (ppm) 7.31 (d, 2H); 7.27 (t, 2H); 7.2 (t, 1H); 7.13 (dd, 1H); 6.91 (dd, 1H); 6.86 (td, 1H); 4.62 (q, 1H); 3.92 (bt, 1H); 3.53 (d, 1H); 3.48 (d, 1H) 3.24 (m, 1H); 2.72 (bm, 2H); 2.64 (m, 1H); 2.5 (m, 2H); 2.19 (s, 3H); 1.27 (s, 9H); 1.21 (d, 3H). MS (ES/+): m/z=457 [M+H]$^+$.

Intermediate 10b

4Benzyl-1-(4-fluoro-2-methyl-phenyl)-piperazine-2-carboxylic acid, 1-(S)-tert-butoxycarbonyl-ethyl ester (diastereoisomer 2)

T.l.c.: CH/Et2O 8:2, Rf=0.37. IR (nujol, cm$^{-1}$): 1746 (C=O). $^1$H-NMR (d$_6$-DMSO): δ (ppm) 7.3–7.25 (m, 4H); 7.23–7.19 (m, 1H); 7.15 (dd, 1H); 6.9 (dd, 1H); 6.83 (td, 1H); 4.66 (q, 1H); 3.85 (m, 1H); 3.59 (d, 1H); 3.49 (m, 1H); 3.42 (d, 1H); 2.85 (dd, 1H); 2.72 (m, 1H); 2.65 (m, 1H); 2.59 (dd, 1H); 2.43 (m, 1H); 2.2 (s, 3H); 1.23 (s, 9H); 1.1 (s, 3H). MS (ES/+): m/z=457 [M+H]$^+$.

Intermediate 11

4-(4-Fluoro-2-methyl-phenyl)-piperazine-1,3-dicarboxylic acid 3-(S)-tert-butoxycarbonyl-ethyl ester 1-tert-butyl ester (diastereoisomer 1)

A mixture of intermediate 10a (343 mg), palladium over charcoal (10%—110 mg) and acetic acid (150 μL) in EtOH (15 mL) was hydrogenated at 6 atm for 16 hours. The catalyst was filtered off and the filtrate was concentrated in vacuo to give 1-(4-fluoro-2-methyl-phenyl)-piperazine-2-carboxylic acid 1-(S)-tert-butoxycarbonyl-ethyl ester (324 mg). Di tert-butyl dicarbonate (211 mg) was added to a solution of 1-(4-fluoro-2-methyl-phenyl)-piperazine-2-carboxylic acid 1-(S)-tert-butoxycarbonyl-ethyl ester (324 mg) and TEA (933 μL) in anhydrous DCM (10 mL), previously cooled to 0° C. under a Nitrogen atmosphere. The solution was allowed to warm to r.t. and stirred at r.t. for 2 hours. The solution was concentrated in vacuo and the residue was purified by flash chromatography (CH/AcOEt 8:2) to give the title compound (250 mg) as a yellow oil.

T.l.c.: CH/AcOEt 8:2, Rf=0.64. $^1$H-NMR ($d_6$-DMSO): δ (ppm) 7.15 (dd, 1H); 6.96 (dd, 1H); 6.89 (td, 1H); 4.72 (q, 1H); 3.87 (m, 1H); 3.74 (m, 1H); 3.7 (m, 1H); 3.55 (m, 1H); 3.43 (m, 1H); 3.24 (m, 1H); 2.7 (m, 1H); 2.28 (s, 3H); 1.42 (s, 9H); 1.36 (s, 9H); 1.25 (d, 3H). MS (ES/+): m/z=467 [M+H]$^+$.

Intermediate 12

4(Fluoro-2-methyl-phenyl)-piperazine-1,3-dicarboxylic acid 1-tert-butyl ester (enantiomer 1)

A solution of lithium hydroxide monohydrate (90 mg) in water (5 mL) was added to a solution of intermediate 11 (250 mg) in MeOH (5 mL) and the resulting solution was heated to 80° C. for 2 hours. The mixture was concentrated in vacuo to half volume, treated with 5% hydrochloric acid solution until pH=5 and extracted with AcOEt. The organic phase was dried and concentrated in vacuo to give the title compound (150 mg) as a white foam.

T.l.c.: CH/AcOEt 1:1, Rf=0.45. $^1$H-NMR ($d_6$-DMSO): δ (ppm) 12.6 (bs, 1H); 7.14 (dd, 1H); 6.96 (dd, 1H); 6.9 (dt, 1H); 3.82–3.72 (bs, 1H); 3.7–3.55 (m, 2H); 3.42–3.34 (m, 3H); 2.62 (m, 1H); 2.27 (s, 3H); 1.42 (s, 9H). MS (ES/+): m/z=339 [M+H]$^+$.

Intermediate 13

3-[(3,5-Dichloro-benzyl)-methylcarbamoyl]-4-(4-fluoro-2-methyl-phenyl)-piperazine-1-carboxylic acid tert-butyl ester (enantiomer 1)

DIPEA (236 μL) and O-(benzotriazol-1-yl)-N,N,N'N'-tetramethyluronium tetrafluoroborate (182 mg) were added to a solution of intermediate 12 (150 mg) in anhydrous DMF (10 mL) under a Nitrogen atmosphere. After stirring for 10 minutes, 3,5-chloro-benzyl-methylamine hydrochloride (110 mg) was added and the mixture was stirred at r.t. for 4 hours. The solution was partitioned between AcOEt (15 mL) and water (15 mL). The organic extracts were washed with water and brine, dried and concentrated in vacuo to a residue, which was purified by flash chromatography (CH/AcOEt 8:2) to give the title compound (167 mg) as a yellow oil.

T.l.c.: AcOEt/CH 1:1, Rf=0.6. MS (ES/+): m/z=510 [M+H]$^+$.

Intermediate 14

4-(4-Fluoro-2-methyl-phenyl)-piperazine-1,3-dicarboxylic acid, 3-(S)-tert-butoxycarbonyl-ethyl ester 1-tert-butyl ester (diastereoisomer 2)

A mixture of intermediate 10b (300 mg), palladium over charcoal (10%—100 mg) and acetic acid (200 μL) in EtOH (20 mL) was hydrogenated at 6 atm for 16 hours. The catalyst was filtered off and the filtrate was concentrated in vacuo to give 14-fluoro-2-methyl-phenyl)-piperazine-1,3-dicarboxylic acid 3-(S)-tert-butoxycarbonyl-ethyl ester, (295 mg). Di tert-butyl dicarbonate (193 mg) was added to a solution of 1-(4-fluoro-2-methyl-phenyl)-piperazine-2-carboxylic acid 1-(S)-tert-butoxycarbonyl-ethyl ester (295 mg) and TEA (788 μL) in anhydrous DCM (8 mL), previously cooled to 0° C. under a Nitrogen atmosphere. The solution was allowed to warm to r.t. and stirred at r.t. for 2 hours. The solution was concentrated in vacuo and the residue was purified by flash chromatography (CH/AcOEt 8:2) to give the title compound (195 mg) as white solid.

T.l.c.: CH/AcOEt 8:2, Rf=0.64. $^1$H-NMR ($d_6$-DMSO): δ (ppm) 7.17 (dd, 1H); 6.96 (dd, 1H); 6.88 (td, 1H); 4.71 (q, 1H); 3.92 (m, 1H); 3.8 (m, 1H); 3.64 (m, 1H); 3.59 (m, 1H); 3.42 (m, 1H); 3.3 (m, 1H); 2.7 (m, 1H); 2.27 (s, 3H); 1.41 (s, 9H); 1.31 (s, 9H); 1.24 (d, 3H). MS (ES/+): m/z=467 [M+H]$^+$.

Intermediate 15

4-(Fluoro-2-methyl-phenyl)-piperazine-1,3-dicarboxylic acid 1-tert-butyl ester (enantiomer 2)

A solution of lithium hydroxide monohydrate (70 mg) in water (4 mL) was added to a solution of intermediate 14 (190 mg) in MeOH (4 mL) and the resulting solution was heated to 80° C. for 2 hours. The mixture was concentrated in vacuo to half volume, treated with 5% hydrochloric acid solution until pH=5 and extracted with AcOEt (4×20 mL). The organic phase was dried and concentrated in vacuo to give the title compound (140 mg) as a white solid.

T.l.c.: CH/AcOEt 1:1 Rf=0.45. $^1$H-NMR ($d_6$-DMSO): δ (ppm) 12.6 (bs, 1H); 7.14 (dd, 1H); 6.96 (dd, 1H); 6.9 (dt, 1H); 3.82–3.72 (bs, 1H); 3.7–3.55 (m, 2H); 3.42–3.34 (m, 3H); 2.62 (m, 1H); 2.27 (s, 3H); 1.42 (s, 9H). MS (ES/+): m/z=339 [M+H]$^+$.

Intermediate 16

3-[(3,5-Dichloro-benzyl-methylcarbamoyl]-4-(4-fluoro-2-methyl-phenyl)-piperazine-1-carboxylic acid tert-butyl ester (enantiomer 2)

DIPEA (225 μL) and O-(benzotriazol-1-yl)-N,N,N'N'-tetramethyluronium tetrafluoroborate (175 mg) were added to a solution of intermediate 15 (140 mg) in anhydrous DMF (10 mL) under a Nitrogen atmosphere. After stirring for 10 minutes, 3,5-dichloro-benzyl-methylamine hydrochloride (103 mg) was added and the mixture was stirred at r.t. for 4.5 hours. The solution was diluted with water (5 mL) and extracted with AcOEt (3×30 mL). The combined organic extracts were washed with brine (3×50 mL), dried and concentrated in vacuo to a residue, which was purified by flash chromatography (CH/AcOEt 7:3) to give the title compound (180 mg) as a white solid.

T.l.c.: AcOEt/CH 1:1, Rf=0.7. $^1$H-NMR ($d_6$-DMSO): δ (ppm) 7.37 (bs, 1H); 7.16 (m, 1H); 6.93 (m, 1H); 6.92 (bs, 2H); 6.83 (m, 1H); 4.59 (d, 1H); 4.3–3.2 (bm, 7H); 2.96 (bs, 3H); 2.57 (m, 1H); 2.29 (bs, 3H); 1.43 (s, 9H). MS (ES/+): m/z=510 [M+H]$^+$.

Intermediate 17

4-Benzyl-1-(4-fluoro-2-methyl-phenyl)-piperazine-2-carboxylic acid (enantiomer 1)

A solution of lithium hydroxide monohydrate (43 mg) in water (2 mL) was added to a solution of intermediate 10a (121 mg) in MeOH (2 mL) and the resulting solution was heated to 80° C. for 2 hours. The mixture was concentrated in vacuo to half volume, treated with 5% hydrochloric acid solution until pH=5 and extracted with AcOEt (4×20 mL). The organic phase was dried and concentrated in vacuo to give the title compound (140 mg) as a white solid.

T.l.c.: CH/AcOEt 1:1 Rf=0.45. $^1$H-NMR (CDCl$_3$): δ (ppm) 7.3 (m, 5H); 7.0 (m, 1H); 6.8 (m, 2H); 3.8–3.6 (m, 5H); 3.2 (m, 1H); 2.9–2.8 (m, 1H); 2.7–2.5 (m, 2H); 2.2 (s, 3H).

Intermediate 18

4-Benzyl-1-(4-fluoro-2-methyl-phenyl)-piperazine-2-carboxylic acid (3,5-bis-trifluoromethyl-benzyl)-methylamide (enantiomer 1)

DIPEA (82 μL) and O-(benzotriazol-1-yl)-N,N,N'N'-tetramethyluronium tetrafluoroborate (63 mg) were added to a solution of intermediate 17 (52 mg) in anhydrous DMF (3.5 mL) under a Nitrogen atmosphere. After stirring for 5 minutes, 3,5-bis(trifluoromethyl)-benzyl-methylamine hydrochloride (49 mg) was added and the mixture was stirred at r.t. for 16 hours. The solution was partitioned between AcOEt and water. The organic extracts were washed with water and brine, dried and concentrated in vacuo to a residue which was purified by flash chromatography (CH/AcOEt 8:2) to give the title compound (56 mg) as yellow oil.

T.l.c.: AcOEt/CH 1:1, Rf=0.61. MS (ES/+): m/z=568 [M+H]$^+$.

Intermediate 19

4-Benzyl-1-(4-fluoro-2-methyl-phenyl)-piperazine-2-carboxylic acid (enantiomer 2)

A solution of lithium hydroxide monohydrate (38 mg) in water (2 mL) was added to a solution of intermediate 10b (107 mg) in MeOH (2 mL) and the resulting solution was heated to 80° C. for 2 hours. The mixture was concentrated in vacuo to half volume, treated with 5% hydrochloric acid solution until pH=5 and extracted with AcOEt (4×20 mL). The organic phase was dried and concentrated in vacuo to give the title compound (76 mg) as a white solid.

T.l.c.: CH/AcOEt 1:1 Rf=45. $^1$H-NMR (CDCl$_3$): δ (ppm) 7.3 (m, 5H); 7.0 (m, 1H); 6.8 (m, 2H); 5.0 (bs, 2H); 3.9–3.7 (m, 4H); 3.0–2.8 (m, 1H); 2.8–2.6 (m, 2H); 2.2 (s, 3H).

Intermediate 20

4-Benzyl-1-(4-fluoro-2-methyl-phenyl)-piperazine-2-carboxylic acid (3,5-bis-trifluoromethyl-benzyl) methylamide (enantiomer 2)

DIPEA (120 μL) and O(benzotriazol-1-yl)-N,N,N'N'-tetramethyluronium tetrafluoroborate (93 mg) were added to a solution of intermediate 19 (76 mg) in anhydrous DMF (5 mL) under a Nitrogen atmosphere. After stirring for 5 minutes, 3,5-bis(trifluoromethyl)-benzyl-methylamine hydrochloride (49 mg) was added and the mixture was stirred at r.t. for 16 hours. The solution was partitioned between AcOEt and water. The organic extracts were washed with water and brine, dried and concentrated in vacuo to a residue which was purified by flash chromatography (CH/AcOEt 8:2) to give the title compound (90 mg) as yellow oil. T.l.c.: AcOEt/CH 1:1, Rf=0.61. $^1$H-NMR (d$_6$-DMSO): δ (ppm) 7.73 (s, 1H); 7.4–7.2 (m, 7H); 7.05 (d, 1H); 6.88–6.7 (m, 2H); 4.7–4.3 (m, 2H); 4.28 (dd, 1H); 3.6 (s, 2H); 2.9 (s, 3H); 3.1–2.4 (m, 6H); 2.32 (s, 3H).

Intermediate 21

3-[(3,5-Dibromo-benzyl)-methylcarbamoyl]-4-(4-fluoro-2-methyl-phenyl)-piperazine-1-carboxylic acid tert-butyl ester DIPEA (0.34 mL) and O-(benzotriazol-1-yl)-N,N,N'N'-tetramethyluronium tetrafluoroborate (257 mg) were added to a solution of intermediate 8 (214 mg) in anhydrous DMF (35 mL) under a Nitrogen atmosphere. After stirring for 5 minutes, 3,5-dibromo-benzyl-methylamine hydrochloride (300 mg) was added and the mixture was stirred at r.t. overnight. The solution was diluted with water and extracted with AcOEt (3×40 mL). The combined organic extracts were washed with brine, dried and concentrated in vacuo to a residue which was purified by flash chromatography (CH/AcOEt 8:2) to give the title compound (316 mg) as yellow oil.

T.l.c.: CH/AcOEt 7:3, Rf=0.51. $^1$H-NMR (d$_6$-DMSO—90° C.): δ (ppm) 7.66 (bs, 1H); 7.18 (dd, 1H); 7.09 (bs, 2H); 6.99 (dd, 1H); 6.88 (m, 1H); 4.8–3.9 (bm, 2H); 4.17 (m, 1H); 3.99–3.68 (2bd, 2H); 3.5–3.1 (bm, 3H); 2.94 (s, 3H); 2.52 (bm, 1H); 2.3 (s, 3H); 1.42 (bs, 9H). MS (ES/+): m/z=598 [M+H]$^+$.

Intermediate 22

3-[(3,4-Dibromo-benzyl)methylcarbamoyl]-4-(4-fluoro-2-methyl-phenyl)-piperazine-1-carboxylic acid tert-butyl ester DIPEA (0.1 mL) and O-(benzotriazol-1-yl)-N,N,N'N'-tetramethyluronium tetrafluoroborate (74 mg) were added to a solution of intermediate 8 (61 mg) in anhydrous DMF (10 mL) under a Nitrogen atmosphere. After stirring for 5 minutes, 3,4-dibromo-benzyl-methylamine hydrochloride (85.4 mg) was added and the mixture was stirred at r.t overnight The solution was diluted with water and extracted three times with AcOEt. The combined organic extracts were washed with brine, dried and concentrated in vacuo to a residue which was purified by flash chromatography (CH/AcOEt 7:3) to give the title compound (94.1 mg) as yellow oil.

T.l.c.: CH/AcOEt 7:3, Rf=0.51. $^1$H-NMR (d$_6$-DMSO—90° C.): δ (ppm) 7.51 (d, 1H); 7.29 (dd, 1H); 7.19 (dd, 1H);

7.0 (dd, 1H); 6.9 (m, 1H); 6.65 (bd, 1H); 4.7–4.0 (2bm, 2H); 4.15 (m, 1H); 3.88–3.68 (2bd, 2H); 3.6–3.1 (bm, 3H); 2.96 (s, 3H); 2.54 (bm, 1H); 2.3 (s, 3H); 1.41 (bs, 9H). MS (ES/+): m/z=598 [M+H]$^+$.

Intermediate 23

3-[1-(R)-(3,5-Bis-trifluoromethyl-phenyl)ethyl]-methylcarbamoyl-4-(4-fluoro-2-methyl-phenyl)-piperazine-1-carboxylic acid tert-butyl ester (23a—diastereoisomer 1)

3-[1-(R)-(3,5-Bis-trifluoromethyl-phenyl)ethyl]-methylcarbamoyl-4-(4-fluoro-2-methyl-phenyl)-piperazine-1-carboxylic acid tert-butyl ester (23b—diastereoisomer 2)

DIPEA (238 µL) and O-(benzotriazol-1-yl)-N,N,N'N'-tetramethyluronium tetrafluoroborate (181 mg) were added to a solution of intermediate 8 (150 mg) in anhydrous DMF (15 mL) under a Nitrogen atmosphere. After stirring for 5 minutes, 1-(R)-[3,5-bis(trifluoromethyl)-phenyl]-ethyl-methylamine hydrochloride (49 mg) was added and the mixture was stirred at r.t. for 5 hours. The solution was partitioned between AcOEt and water. The organic extracts were washed with brine, dried and concentrated in vacuo to a residue which was purified by flash chromatography (CH/AcOEt 8:2) to give intermediate 23a (diastereoisomer 1—35 mg) as yellow oil intermediate 23b (diastereoisomer 2—40 mg) as yellow oil.

Intermediate 23a

T.l.c.: AcOEt/CH 1:1, Rf=0.75. $^1$H-NMR (CDCl$_3$—50° C.): δ (ppm) 7.71 (s, 1H); 7.55 (s, 2H); 7.03 (m, 1H); 6.9 (dd, 1H); 6.8 (m, 1H); 5.87 (m, 1H); 4.7–3.8 (2m, 3H); 3.5–3.2 (m, 3H); 2.74 (s, 3H); 2.6 (m, 1H); 2.37 (s, 3H); 1.47 (s, 9H); 1.33 (s, 3H). MS (ES/+): m/z=592 [M+H]$^+$, 614 [M+Na]$^+$.

Intermediate 23b

T.l.c.: AcOEt/CH 1:1, Rf=0.71. MS (ES/+): m/z=592 [M+H]$^+$, 614 [M+Na]$^+$.

Intermediate 24

3-(3-Chloro-4-fluoro-benzyl)-methylcarbamoyl-4-(4-fluoro-2-methyl-phenyl)-piperazine-1-carboxylic acid tert-butyl ester DIPEA (80 µL) and O-(benzotriazol-1-yl)-N,N,N'N'-tetramethyluronium tetrafluoroborate (60 mg) were added to a solution of intermediate 8 (50 mg) in anhydrous DMF (5 mL) under a Nitrogen atmosphere. After stirring for 5 minutes, (3-chloro-4-fluoro-benzyl)-methylamine hydrochloride (32.5 mg) was added and the mixture was stirred at r.t. overnight. The solution was partitioned between AcOEt and water. The organic extracts were washed with brine, dried and concentrated in vacuo to a residue which was purified by flash chromatography (CH/AcOEt 1:1) to give the title compound (43 mg) as yellow oil.

T.l.c.: AcOEt/CH 1:1, Rf=0.45. MS (ES/+): m/z=494 [M+H]$^+$.

Intermediate 25

3-(2,5-Dichloro-benzyl)methylcarbamoyl-4-(4-fluoro-2-methyl-phenyl)-piperazine-1-carboxylic acid tert-butyl ester DIPEA (80 µL) and O-(benzotriazol-1-yl)-N,N,N'N'-tetramethyluronium tetrafluoroborate (60 mg) were added to a solution of intermediate 8 (50 mg) in anhydrous DMF (5 mL) under a Nitrogen atmosphere. After stirring for 5 minutes, 2,5-dichloro-benzyl-methylamine hydrochloride (35 mg) was added and the mixture was stirred at r.t. for 5 hours. The solution was partitioned between AcOEt and water. The organic extracts were washed with brine, dried and concentrated in vacuo to a residue which was purified by flash chromatography (CH/AcOEt 9:1) to give the title compound (50 mg) as yellow oil.

T.l.c.: AcOEt/CH 1:1, Rf=0.61. MS (ES/+): m/z=510 [M+H]$^+$.

Intermediate 26

3-(3-Fluoro-5-trifluoromethyl-benzyl)-carbamoyl-4-(4-fluoro-2-methyl-phenyl)-piperazine-1-carboxylic acid tert-butyl ester DIPEA (80 µL) and O-(benzotriazol-1-yl)-N,N,N'N'-tetramethyluronium tetrafluoroborate (60 mg) were added to a solution of intermediate 8 (50 mg) in anhydrous DMF (5 mL) under a Nitrogen atmosphere. After stirring for 5 minutes, (3-fluoro-5-trifluoromethyl)-benzylamine (30 mg) was added and the mixture was stirred at r.t. overnight. The solution was partitioned between AcOEt and water. The organic extracts were washed with brine, dried and concentrated in vacuo to a residue which was purified by flash chromatography (CH/AcOEt 8:2) to give the title compound (61 mg) as yellow oil.

$^1$H-NMR (d$_6$-DMSO): δ (ppm) 8.3 (t, 1H); 7.43 (d, 1H); 7.19 (s, 1H); 7.11 (dd, 1H); 6.94 (dd, 1H); 6.83 (td, 1H); 6.67 (d, 1H); 4.2 (m, 2H); 3.94 (m, 1H); 3.74 (d, 1H); 3.67 (dd, 1H); 3.3–3.0 (m, 3H); 2.28 (s, 3H); 2.42 (m, 1H); 1.4 (s, 9H). MS (ES/+): m/z=514 [M+H]$^+$, 536 [M+Na]$^+$.

Intermediate 27

3(3-Fluoro-5-trifluoromethyl-benzyl)methylcarbamoyl-4-(4-fluoro-2-methyl-phenyl)-piperazine-1-carboxylic acid tert-butyl ester Sodium hydride (60% suspension in mineral oil—7 mg) was added to a solution of intermediate 26 (60 mg) in anhydrous THF (2.5 mL). The suspension was stirred at r.t. for 10 minutes, then methyl iodide (22 µL) was added. The mixture was heated in a sealed tube at 50° C. for 5 hours, adding further sodium hydride (9.4 mg) and methyl iodide (36.4 µL) during this time. After cooling to r.t., water was added and the mixture was extracted with AcOEt. The organic extract was dried and concentrated in vacuo to give the title compound (62 mg) as a yellow oil.

T.l.c.: AcOEt/CH 7:3, Rf=0.54. MS (ES/+): m/z=528 [M+H]$^+$.

Intermediate 28

N-Benzyl-2-(2,4-difluoro-phenylamino)-acetamide

A mixture of N-benzyl-2-chloroacetamide (700 mg—obtained as described for intermediate 1), DIPEA (0.76 mL) and 2,4-difluoro-aniline (0.4 mL) in anhydrous DMF (5 mL)

was stirred at 100° C. for 40 hours under a Nitrogen atmosphere. Then, more DIPEA (0.2 mL) was added and the mixture was heated to 100° C. for further 4 hours. After cooling to room temperature, the solution was diluted with AcOEt and washed with water and ice. The separated aqueous phase was extracted with further AcOEt (3×20 mL). The combined organic extracts were dried and concentrated in vacuo. The residue was purified by flash chromatography (CH/AcOEt 7:3) to give the title compound (600 mg) as a beige solid.

T.l.c.: AcOEt/CH 1:1, Rf=0.39. $^1$H-NMR (d$_6$-DMSO): δ (ppm) 8.45 (bt, 1H); 7.26 (t, 2H); 7.2 (m, 3H); 7.09 (dd, 1H); 6.86 (dd, 1H); 6.52 (td, 1H); 5.68 (bt, 1H); 4.28 (d, 2H); 3.73 (d, 2H). MS (ES/+): m/z=277 [+H]$^+$.

Intermediate 29

N-Benzyl-N'-(2,4-difluoro-phenyl)-1,2-ethylenediamine

Borane (1M solution in THF, 17 mL) was added dropwise at r.t. to a solution of intermediate 28 (586 mg) in anhydrous THF (30 mL) under a Nitrogen atmosphere. The mixture was heated to reflux for 4 hours, then it was cooled to 0° C. and a 10% hydrochloric acid solution (15 mL) was added. The mixture was stirred at r.t. overnight. Then, it was basified with solid potassium hydroxide and extracted with AcOEt. The organic phase was washed with water. The aqueous phase was extracted with further AcOEt (3×30 mL). The combined organic extracts were concentrated in vacuo to give the title compound (535 mg) as an orange oil.

$^1$H-NMR (CDCl$_3$): δ (ppm) 7.31 (m, 5H); 6.78 (m, 1H); 6.74 (m, 1H); 6.61 (m, 1H); 4.2 (bt, 1H); 3.83 (s, 2H); 3.21 (bt, 2H); 2.93 (m, 2H). MS (ES/+): m/z=263 [M+H]$^+$.

Intermediates 30

4-Benzyl-1-(2,4-difluoro-phenyl)-piperazine-2-carboxylic acid ethyl ester

A solution of intermediate 29 (535 mg) and DIPEA (1.16 mL) in toluene (7 mL) was added to a solution of ethyl 2,3-dibromopropionate (0.6 mL) in toluene (13 mL) previously heated at 50° C. under a Nitrogen atmosphere. The mixture was then stirred at 100° C. for 32 hours. The mixture was cooled to r.t., then diluted with AcOEt and toluene and washed with water. The separated organic phase was concentrated in vacuo and the residue was purfied by flash chromatography (CH/AcOEt 95:5) to give the title compound (183 mg) as a yellow oil.

T.l.c.: CH/AcOEt 9:1, Rf=32. $^1$H-NMR (d$_6$DMSO): δ (ppm) 7.3 (m, 5H); 7.08 (m, 1H); 6.8 (m, 1H); 6.76 (m, 1H); 4.21 (m, 1H); 4.07 (m, 2H); 3.81 (dt, 1H); 3.64 (d, 1H); 3.46 (d, 1H); 3.23 (m, 1H); 3.0 (m, 1H); 2.89 (m, 1H); 2.56 (dd, 1H); 2.43 (dt, 1H); 1.14 (t, 3H). MS (ES/+): m/z=361 [M+H]$^+$.

Intermediate 31

1-(2,4-Difluoro-phenyl)-piperazine-2-carboxylic acid ethyl ester

A mixture of the intermediate 30 (183 mg) in EtOH (20 mL) containing glacial acetic acid (0.2 mL) and 10% palladium on carbon (80 mg) was stirred under hydrogen at 5 atm. for 20 hours. The mixture was filtered through a pad of celite, and the filtrate was concentrated in vacuo to give the title compound (160 mg) as a yellow oil.

$^1$H-NMR (CDCl$_3$): δ (ppm) 7.0 (m, 1H); 6.8 (m, 2H); 4.14 (bs, 1H); 4.08 (q, 2H); 3.7–3.5 (m, 2H); 3.45–2.9 (m, 5H); 1.15 (t, 3H). MS (ES/+): m/z=271 [M+H]$^+$.

Intermediate 32

4-(2,4-Difluoro-phenyl)-piperazine-1,3-dicarboxylic acid 1-tert-butyl ester 3-ethyl ester Di-tert-butyl-dicarbonate (142 mg) and TEA (0.25 mL) were added to a solution of intermediate 31 (160 mg) in anhydrous DCM (16 mL) under a Nitrogen atmosphere. The solution was stirred at r.t. for 5 hours, then it was washed with brine. The organic layer was dried and concentrated in vacuo to give the title compound (155 mg) as a yellow oil.

T.l.c.: CH/AcOEt 1:1, Rf=0.70. MS (ES/+): m/z=371 [M+H]$^+$.

Intermediate 33

4-(2,4-Difluoro-phenyl)-piperazine-1,3-dicarboxylic acid 1-tert-butyl ester

A solution of lithium hydroxide hydrate (143 mg) in water (2 mL) was added to a solution of intermediate 32 (1.2 g) in MeOH (16 mL). The mixture was heated to 70° C. for 4 hours. The solution was allowed to cool to r.t., neutralised with 1N hydrochloric acid solution until pH=5 and extracted with DCM. The organic layer was dried and concentrated in vacuo to give the title compound (120 mg) as pale yellow solid.

T.l.c.: CH/AcOEt 1:1, Rf=0.19. $^1$H-NMR (CDCl$_3$): δ (ppm) 7.7 (m, 2H); 7.0 (d, 1H); 4.4 (d, 1H); 4.2–3.7 (s+t, 2H); 4.1–3.5 (m+d, 2H); 3.1–2.9 (m+d, 2H); 1.4 (s, 9H).

Intermediate 34

3-[(3,5-Dichloro-benzyl)-methylcarbamoyl]-4-(2,4-difluoro-phenyl)-piperazine-1-carboxylic acid tert-butyl ester DIPEA (0.113 mL) and O-(benzotriazol-1-yl)-N,N,N'N'-tetramethyluronium tetrafluoroborate (75 mg) were added to a solution of intermediate 33 (61.5 mg) in anhydrous DMF (7 mL) under a Nitrogen atmosphere. After stirring for 5 minutes, 3,5-dichloro-benzyl-methylamine hydrochloride (49.8 mg) was added and the mixture was stirred at r.t. for 5 hours. The solution was partitioned between AcOEt and water. The separated aqueous phase was further extracted with AcOEt. The combined organic extracts were washed with brine, dried and concentrated in vacuo to give the title compound (93 mg) as yellow oil.

T.l.c.: AcOEt/CH 6:4, Rf=0.89. MS (ES/+): m/z=514 [M+H]$^+$.

Intermediate 35

3-[(3,5-Bis-trifluoromethyl-benzyl)-methylcarbamoyl]-4-(2,4-difluoro-phenyl)-piperazine-1-carboxylic acid tert-butyl ester DIPEA (0.13 mL) and O-(benzotriazol-1-yl)-N,N,N'N'-tetramethyluronium tetrafluoroborate (73 mg) were added to a solution of intermediate 33 (60 mg) in anhydrous DMF (7 mL) under a Nitrogen atmosphere. After stirring for 5 minutes, 3,5-bis(trifluoromethyl)-benzyl-methylamine hydrochloride (55 mg) was added and the mixture was stirred at r.t. for 5 hours. The solution was partitioned between AcOEt and water. The separated aqueous phase was further extracted with AcOEt. The combined organic extracts were washed with brine, dried and concentrated in vacuo to give the title compound (115 mg) as yellow oil.

T.l.c.: AcOEt/CH 6:4, Rf=0.70. MS (ES/+): m/z=582 [M+H]$^+$.

Intermediate 36

N-Benzyl-2-(2,4,6-trifluoro-phenylamino)-acetamide

A mixture of N-benzyl-2-chloroacetamide (700 mg—obtained as described for intermediate 1), DIPEA (0.76 mL) and 2,4,6-trifluoro-aniline (559 mg) in anhydrous DMF (5 mL) was stirred at 100° C. for 40 hours under a Nitrogen atmosphere. Then, more DIPEA (0.2 mL) was added and the mixture was heated to 100° C. for further 4 hours. After cooling to room temperature, the solution was diluted with AcOEt and washed with water and ice. The separated aqueous phase was extracted with further AcOEt (3×30 mL). The combined organic extracts were dried and concentrated in vacuo. The residue was purified by flash chromatography (CH/AcOEt from 8:2 to 6:4) to give the title compound (265 mg) as a beige solid.

T.l.c.: AcOEt/CH 1:1, Rf=0.45. $^1$H-NMR (d$_6$-DMSO): δ (ppm) 7.34–7.29 (m, 5H); 6.9 (bm, 1H); 6.66 (m, 2H); 4.53 (d, 2H); 4.0 (bm, 1H); 3.9 (d, 2H). MS (ES/+): m/z=295 [M+H]$^+$.

Intermediate 37

N-Benzyl-N'-(2,4,6-trifluoro-phenyl)-1,2-ethylenediamine

Borane (1M solution in THF, 7.2 mL) was added dropwise at r.t. to a solution of intermediate 36 (265 mg) in anhydrous THF (13 mL) under a Nitrogen atmosphere. The mixture was heated to reflux for 4 hours, then it was cooled to 0° C. and a 10% hydrochloric acid solution was added. The mixture was stirred at r.t. overnight. Then, it was basified with solid potassium hydroxide, diluted with water and extracted with DCM. The organic phase was washed with water. The aqueous phase was extracted with DCM (3×20 mL). The combined organic extracts were concentrated in vacuo to give the tide compound (216 mg) as an orange oil.

$^1$H-NMR (CDCl$_3$): δ (ppm) 7.28 (m, 4H); 7.2 (m, 1H); 7.03 (t, 2H); 4.62 (m, 1H); 3.66 (s, 2H); 3.2 (q, 2H); 2.63 (t, 2H); 2.22 (bs, 1H). MS (ES/+): m/z=281 [M+H]$^+$.

Intermediates 38

4-Benzyl-1-(2,4,6-trifluoro-phenyl)-piperazine-2-carboxylic acid ethyl ester

A solution of intermediate 37 (216 mg) and DIPEA (0.44 mL) in toluene (2.5 mL) was added to a solution of ethyl 2,3-dibromopropionate (0.22 mL) in toluene (8 mL) previously heated at 50° C. under a Nitrogen atmosphere. The mixture was then stirred at 100° C. for 32 hours. The mixture was cooled to r.t., then diluted with AcOEt and toluene and washed with water. The separated organic phase was concentrated in vacuo and the residue was purified by flash chromatography (CH/AcOEt 95:5) to give the title compound (57 mg) as a yellow oil.

T.l.c.: CH/AcOEt 9:1, Rf=0.36. $^1$H-NMR (d$_6$-DMSO): δ (ppm) 7.31 (m, 5H); 6.61 (m, 2H); 4.11 (m, 2H); 4.02 (t, 1H); 3.8 (m, 1H); 3.62 (d, 1H); 3.49 (d, 1H); 3.08 (m, 2H); 2.74 (m, 1H); 2.62 (dd, 1H); 2.41 (m, 1H); 1.17 (t, 3H). MS (ES/+): m/z=379 [M+H]$^+$.

Intermediate 39

1-(2,4,6-Trifluoro-phenyl)-piperazine-2-carboxylic acid ethyl ester

A mixture of the intermediate 38 (57 mg) in EtOH (8 mL) containing glacial acetic acid (60 μL) and 10% palladium on carbon (24 mg) was stirred under hydrogen at 5 atm. for 20 hours. The mixture was filtered through a pad of celite, and the filtrate was concentrated in vacuo to give the title compound (53 mg) as a yellow oil.

T.l.c.: AcOEt/MeOH 8:2, Rf=0.3. MS (ES/+): m/z=289 [+H]$^+$.

Intermediate 40

4-(2,4,6-Trifluoro-phenyl)-piperazine-1,3-dicarboxylic acid 1-tert-butyl ester 3-ethyl ester Di-tert-butyl-dicarbonate (44 mg) and TEA (77 μL) were added to a solution of intermediate 39 (53 mg) in anhydrous DCM (5 mL) under a Nitrogen atmosphere. The solution was stirred at r.t. for 5 hours, then it was washed with brine. The organic layer was dried and concentrated in vacuo to give the title compound (67 mg) as a yellow oil.

T.l.c.: CH/AcOEt 1:1, Rf=0.75.

Intermediate 41

4-(2,4,6-Trifluoro-phenyl)-piperazine-1,3-dicarboxylic acid 1-tert-butyl ester

A solution of lithium hydroxide hydrate (43 mg) in water (0.5 mL) was added to a solution of intermediate 40 (67 mg) in MeOH (4 mL). The mixture was heated to 70° C. for 4 hours. The solution was allowed to cool to r.t., neutralised with 1N hydrochloric acid solution until pH=5 and extracted with DCM. The organic layer was dried and concentrated in vacuo to give the title compound (50 mg) as pale yellow solid.

T.l.c.: CH/AcOEt 1:1, Rf=0.2.

Intermediate 42

3-[(3,5-Dichloro-benzyl)-methylcarbamoyl]-4-(2,4,6-trifluoro-phenyl)-piperazine-1-carboxylic acid tert-butyl ester DIPEA (38 μL) and O-(benzotriazol-1-yl)-N,N,N'N'-tetramethyluronium tetrafluoroborate (29 mg) were added to a solution of intermediate 41 (25 mg) in anhydrous DMF (3 mL) under a Nitrogen atmosphere. After stirring for 5 minutes, 3,5-dichloro-benzyl-methylamine hydrochloride (18 mg) was added and the mixture was stirred at r.t. for 5 hours. The solution was partitioned between AcOEt and water. The separated aqueous phase was further extracted with AcOEt The combined organic extracts were washed with brine, dried and concentrated in vacuo to give the title compound (25 mg) as yellow oil.

T.l.c.: AcOEt/CH 1:1, Rf=0.89.

Intermediate 43

3-[(3,5-Bis-trifluoromethyl-benzyl)-methylcarbamoyl]-4-(2,4,6-trifluoro-phenyl)-piperazine-1-carboxylic acid tert-butyl ester DIPEA (38 µL) and O-(benzotriazol-1-yl)-N,N,N'N'-tetramethyluronium tetrafluoroborate (29 mg) were added to a solution of intermediate 41 (25 mg) in anhydrous DMF (3 mL) under a Nitrogen atmosphere. After stirring for 5 minutes, 3,5-(bis-trifluoromethyl)-benzyl-methylamine hydrochloride (18 mg) was added and the mixture was stirred at r.t. for 5 hours. The solution was partitioned between AcOEt and water. The separated aqueous phase was further extracted with AcOEt. The combined organic extracts were washed with brine, dried and concentrated in vacuo to give the title compound (31 mg) as yellow oil.
T.l.c.: AcOEt/CH 1:1, Rf=0.8.

Intermediate 44

N-Benzyl-2-(4-fluoro-phenylamino)-acetamide

A mixture of N-benzyl-2-chloroacetamide (8.3 g—obtained as described for intermediate 1), DIPEA (9.31 mL) and 4-fluoro-aniline (4.28 mL) in anhydrous DMF (60 mL) was stirred at 100° C. for 24 hours under a Nitrogen atmosphere and then left at r.t. for two days. The solution was poured into water (100 mL) and extracted with AcOEt (2×200 mL). The combined organic extracts were washed with brine (100 mL), dried and concentrated in vacuo. The residue was purified by flash chromatography (CH/AcOEt 7:3) to give the title compound (7.73 g) as a beige solid.
$^1$H-NMR (CDCl$_3$): δ (ppm) 7.2 (m, 5H); 7.0 (bs, 1H); 6.8 (t, 2H); 6.5 (dd, 2H); 4.4 (d, 2H); 4.2 (bs, 1H); 3.8 (d, 2H).

Intermediate 45

N-Benzyl-N'-(4-fluoro-phenyl)-1,2-ethylenediamine

Borane (1M solution in THF, 112 mL) was added dropwise at r.t. to a solution of intermediate 44 (3.7 g) in anhydrous THF (200 mL) under a Nitrogen atmosphere. The mixture was heated to reflux for 4 hours, then it was cooled to 0° C. and a 10% hydrochloric acid solution (50 mL) was added. The mixture was stirred at r.t. for 8 hours. Then, it was extracted three times with AcOEt The combined organic extracts were dried and concentrated in vacuo. The residue was diluted with water and basified with solid potassium hydroxide. The solution was with DCM. The combined organic extracts were concentrated in vacuo to give the title compound (2.84 g) as an orange oil.
$^1$H-NMR (CDCl$_3$): δ (ppm) 7.3 (m, 5H); 6.8 (t, 2H); 6.5 (dd, 2H); 3.8 (s, 2H); 3.2 (t, 2H); 2.8 (t, 2H).

Intermediates 46

4-Benzyl-1-(4-fluoro-phenyl)-piperazine-2-carboxylic acid ethyl ester

A solution of intermediate 45 (2.81 g) and DIPEA (6.59 mL) in toluene (40 mL) and DMF (5 mL) was added to a solution of ethyl 2,3-dibromopropionate (3.34 mL) in toluene (70 mL) previously heated at 50° C. under a Nitrogen atmosphere. The mixture was then stirred at 100° C. for 22 hours. The mixture was cooled to r.t., then diluted with AcOEt and toluene and washed with water. The separated organic phase was concentrated in vacuo and the residue was purified by flash chromatography (CH/AcOEt 95:5) to give the title compound (1.18 g) as a yellow oil.
T.l.c.: CH/AcOEt 95:5, Rf=0.62. $^1$H-NMR (d$_6$-DMSO): δ (ppm) 7.31–7.27 (m, 5H); 6.94 (m, 2H); 6.81 (m, 2H); 4.33 (m, 1H); 4.08 (m, 2H); 3.65 (d, 1H); 3.59 (td, 1H); 3.45 (d, 1H); 3.29 (m, 2H); 2.95 (m, 1H); 2.47 (dd, 1H); 2.37 (dt, 1H); 1.12 (t, 3H). MS (ES/+): m/z=343 [M+H]$^+$.

Intermediate 47

4-Benzyl-1-(4-fluoro-phenyl)-piperazine-2-carboxylic acid (3,5-bis-trifluoromethyl-benzyl-methylamide Lithium hydroxide hydrate (46 mg) was added to a solution of intermediate 46 (94 mg) in MeOH (8 mL) and water (1 mL) and the resulting solution was stirred at 70° C. for 5 hours. The solution was allowed to cool to r.t., neutralized with 1N hydrochloric acid and extracted with DCM and AcOEt. The combined organic extracts were dried and concentrated in vacuo to give 4-benzyl-1-(4-fluoro-phenyl)-piperazine-2-carboxylic acid (88 mg) which was used for the next step without any purification.

DIPEA (147 µL) and O-(benzotriazol-1-yl)-N,N,N'N'-tetramethyluronium tetrafluoroborate (112 mg) were added to a solution of 4-benzyl-1-(4-fluoro-phenyl)-piperazine-2-carboxylic acid (88 mg) in anhydrous DMF (10 mL) under a Nitrogen atmosphere. After stirring for 5 minutes, 3,5-bis (trifluoromethyl)-benzyl-methylamine hydrochloride (85 mg) was added and the mixture was stirred at r.t over week end. The solution was diluted with water and extracted twice with AcOEt. The combined organic extracts were washed with brine, dried and concentrated in vacuo to a residue which was purified by flash chromatography (CH/AcOEt 7:3) to give the title compound (77 mg) as yellow oil.
T.l.c.: AcOEt/CH 6:4, Rf=0.57. IR (film, cm$^{-1}$): 1652 (C=O). $^1$H-NMR (d$_6$-DMSO): δ (ppm) 7.98 (s, 1H); 7.76 (s, 2H); 7.35–7.2 (m, 5H); 6.93 (m, 2H); 6.83 (m, 2H); 4.9 (bs, 1H); 4.83 (d, 1H); 4.34 (d, 1H); 3.68 (m, 1H); 3.58 (d, 1H) 3.47 (d, 1H); 3.28 (m, 1H); 3.04 (m, 1H); 2.86 (m, 1H); 2.91 (s, 3H); 2.43 (dd, 1H); 2.25 (td, 1H). MS (ES/+): m/z=554 [M+H]$^+$.

Intermediate 48

1-(4-Fluoro-phenyl)-piperazine-2-carboxylic acid ethyl ester

A mixture of the intermediate 46 (1.09 g) in EtOH (100 mL) containing glacial acetic acid (1 mL) and 10% palladium on carbon (400 mg) was stirred under hydrogen at 5 atmospheres for 19 hours. The mixture was filtered through a pad of celite, and the filtrate was concentrated in vacua. The crude was dissolved in AcOEt and washed with a 5% sodium hydrogen carbonate solution. the organic layer was dried and concentrated in vacuo to give the title compound (651 mg) as a yellow oil.
T.l.c.: AcOEt/MeOH 8:2, Rf=0.16. $^1$H-NMR (CDCl$_3$): δ (ppm) 7.0 (m, 2H); 6.9 (m, 2H); 4.3 (s, 1H); 4.2 (q, 2H); 3.4 (m, 2H); 3.2–3.0 (2m, 4H); 1.2 (t, 3H).

Intermediate 49

4-(4-Fluoro-phenyl)-piperazine-1,3-dicarboxylic acid 1-tert-butyl ester 3-ethyl ester Di-tert-butyl-dicarbonate (457 mg) and TEA (663 µL) were added to a solution of intermediate 48 (651 mg) in anhydrous DCM (30 mL) under a Nitrogen atmosphere. The solution was stirred at r.t. for 24 hours, then further di-tert-butyl-dicarbonate (207 mg) and TEA (265 µL) were added. The solution was stirred for further 24 hours, then it was washed with water. The organic layer was dried and concentrated in vacuo to a crude, which was purified by flash chromatography (CH/AcOEt 7:3) to give the title compound (908 mg) as a yellow oil.

T.l.c.: AcOEt/MeOH 8:2, Rf=0.89. $^1$H-NMR (CDCl$_3$): δ (ppm) 6.9 (m, 2H); 6.8 (m, 2H); 4.4 (d, 1H); 4.2–4.0 (m, 2H); 4.0 (m, 2H); 3.6–3.2 (m, 2H); 3.2–3.0 (m, 2H); 1.4 (s, 9H); 1.2 (t, 3H).
MS (ES/+): m/z=353 [M+H]$^+$.

Intermediate 50

4-(4-Fluoro-phenyl)-piperazine-1,3-dicarboxylic acid 1-tert-butyl ester

A solution of lithium hydroxide hydrate (537 mg) was added to a solution of intermediate 49 (750 mg) in MeOH (48 mL) and water (8 mL). The mixture was heated to 80° C. for 4 hours. The solution was allowed to cool to r.t., neutralised with 1N hydrochloric acid solution until pH=7 and extracted with AcOEt. The organic layer was dried and concentrated in vacuo to give the title compound (610 mg) as pale yellow solid.

$^1$H-NMR (CDCl$_3$): δ (ppm) 7.0 (t, 2H); 6.8 (dd, 2H); 4.4–4.2 (m, 2H); 4.0 (m, 1H); 3.5–3.2 (m, 4H); 1.4 (s, 9H).

Intermediate 51

3-[(3,5-Dichloro-benzyl)methylcarbamoyl]-4-(4-fluoro-phenyl)-piperazine-1-carboxylic acid tert-butyl ester DIPEA (116 µL) and O-(benzotriazol-1-yl)-N,N,N'N'-tetramethyluronium tetrafluoroborate (104 mg) were added to a solution of intermediate 50 (70 mg) in anhydrous DMF (15 mL) under a Nitrogen atmosphere. After stirring for 5 minutes, 3,5-dichloro-benzyl-methylamine hydrochloride (73 mg) was added and the mixture was stirred at r.t. overnight. The solution was partitioned between AcOEt and water. The separated aqueous phase was further extracted with AcOEt. The combined organic extracts were washed with brine, dried and concentrated in vacuo to a crude, which was purified by flash chromatography (CH/AcOEt 1:1) to give the title compound (65 mg) as yellow oil.

T.l.c.: AcOEt/CH 1:1, Rf=0.61. MS (ES/+): m/z=97 [M+H]$^+$.

Intermediate 52

N-Benzyl-2-(4-triuoromethyl-phenylamino)-acetamide

A mixture of N-benzyl-2-chloroacetamide (0.7 g—obtained as described for intermediate 1), DIPEA (0.78 mL) and 4-trifluoromethyl-aniline (0.48 mL) in anhydrous DMF (7 mL) was stirred at 100° C. for 70 hours under a Nitrogen atmosphere. The solution was poured into water and extracted twice with AcOEt. The combined organic extracts were washed with brine, dried and concentrated in vacuo. The residue was purified by flash chromatography (CH/AcOEt 7:3) to give the title compound (1.85 g).

$^1$H-NMR (CDCl$_3$): δ (ppm) 7.45–7.4 (d, 2H); 7.3–7.15 (m, 5H); 6.7 (bm, 1H); 6.6 (d, 2H); 4.6 (bm, 1H); 4.45 (d, 2H); 3.85 (d, 2H).

Intermediate 53

N-Benzyl-N'-(4-trifluoromethyl-phenyl)-1,2-ethylenediamine

Borane (1M solution in THF, 14.9 mL) was added dropwise at r.t. to a solution of intermediate 52 (0.57 g) in anhydrous THF (24 mL) under a Nitrogen atmosphere. The mixture was heated to reflux for 3 hours, then it was cooled to 0° C. and a 10% hydrochloric acid solution was added. The mixture was stirred at r.t. for overnight. Then, it was extracted three times with AcOEt. The combined organic extracts were dried and concentrated in vacuo. The residue was diluted with water and basified with solid potassium hydroxide. The solution was extracted twice with DCM. The combined organic extracts were concentrated in vacuo to give the title compound (0.45 g) as a yellow oil.

$^1$H-NMR (CDCl$_3$): δ (ppm) 7.45–7.25 (m, 7H); 6.68 (d, 2H); 4.55 (bm, 1H); 3.75 (s, 2H); 3.21 (q, 2H); 2.92 (m, 2H).
MS (ES/+): m/z=295 [+H]$^+$.

Intermediate 54

4-Benzyl-1-(4-trifluoromethyl-phenyl)-piperazine-2-carboxylic acid ethyl ester

A solution of intermediate 53 (0.43 g) and DIPEA (0.84 mL) in toluene (4 mL) was added to a solution of ethyl 2,3-dibromopropionate (0.425 mL) in toluene (10 mL) previously heated to 50° C. under a Nitrogen atmosphere. The mixture was then stirred at 100° C. for 40 hours. The mixture was cooled to r.t., then diluted with AcOEt and toluene and washed with water. The separated organic phase was concentrated in vacuo and the residue was purified by flash chromatography (CH/AcOEt 95:5) to give the title compound (183 mg).

T.l.c.: CH/AcOEt 9:1, Rf=0.30. $^1$H-NMR (d$_6$-DMSO): δ (ppm) 7.45 (d, 2H); 7.35–7.26 (m, 5H); 6.84 (d, 2H); 4.47 (t, 1H); 4.11 (m, 2H); 3.65 (d, 1H); 3.53 (m, 2H); 3.45 (d, 1H); 3.37 (m, 1H); 3.0 (m, 1H); 2.41 (dd, 1H); 2.32 (m, 1H); 1.13 (t, 3H). MS (ES/+): m/z=393 [M+H]$^+$.

Intermediate 55

1-(4-Trifluoromethyl-phenyl)-piperazine-2-carboxylic acid ethyl ester

A mixture of the intermediate 54 (180 mg) in EtOH (16.7 mL) containing glacial acetic acid (0.17 mL) and 10% palladium on carbon (67 mg) was stirred under hydrogen at 5 atmospheres for 20 hours. The mixture was filtered through a pad of celite, and the filtrate was concentrated in vacuo to give the title compound (163 mg).

T.l.c.: AcOEt/MeOH 8:2, Rf=0.44.
MS (ES/+): m/z=303 [M+H]$^+$.

Intermediate 56

4-(4-Trifluoromethyl-phenyl)-piperazine-1,3-dicarboxylic acid 1-tert-butyl ester 3-ethyl ester Di-tert-butyl-dicarbonate (127 mg) and TEA (185 μL) were added to a solution of intermediate 55 (160 mg) in anhydrous DCM (14 mL) under a Nitrogen atmosphere. The solution was stirred at r.t. for 3 hours, then it was concentrated in vacuo to a crude, which was purified by flash chromatography (CH/AcOEt 6:4) to give the title compound (280 mg).

T.l.c.: AcOEt/CH 8:2, Rf=0.90. $^1$H-NMR ($d_6$-DMSO): δ (ppm) 7.45 (d, 2H); 6.85 (d, 2H); 4.6 (bd, 1H); 4.4 (s, 1H); 4.2–4.05 (bm, 3H); 3.53 (bm, 2H); 3.3 (bd, 1H); 3.1 (m, 1H); 1.5 (s, 9H); 1.2 (t, 3H). MS (ES/+): m/z=425 [M+Na]$^+$.

Intermediate 57

4-(4-Trifluoromethyl-phenyl)-piperazine-1,3-dicarboxylic acid 1-tert-butyl ester A solution of lithium hydroxide hydrate (175 mg) was added to a solution of intermediate 56 (750 mg) in MeOH (14 mL) and water (3 mL). The mixture was heated to 80° C. for 2 hours. The solution was allowed to cool to r.t, neutralised with 1N hydrochloric acid solution until pH=7 and extracted with DCM. The organic layer was dried and concentrated in vacuo to give the title compound (125 mg).

$^1$H-NMR (CDCl$_3$): δ (ppm) 7.45 (d, 2H); 6.8 (m, 2H); 4.55 (d, 1H); 4.3 (bm, 1H); 4.05 (bm, 1H); 3.45 (bm, 2H); 2.9 (bm, 2H); 1.37 (s, 9H). MS (ES/+): m/z=397 [M+Na]$^+$.

Intermediate 58

3-[(3,5-Dichloro-benzyl)-methylcarbamoyl]-4-(4-trifluoromethyl-phenyl)-piperazine-1-carboxylic acid tert-butyl ester DIPEA (84 μL) and O-(benzotriazol-1-yl)-N,N,N'N'-tetramethyluronium tetrafluoroborate (67 mg) were added to a solution of intermediate 57 (60 mg) in anhydrous DMF (7 mL) under a Nitrogen atmosphere. After stirring for 1 hour, 3,5-dichloro-benzyl-methylamine hydrochloride (40 mg) was added and the mixture was stirred at r.t. for 3 hours. The solution was partitioned between AcOEt and water. The organic extracts was washed with brine, dried and concentrated in vacuo to a crude, which was purified by flash chromatography (CH/AcOEt 7:3) to give the title compound (61 mg).

$^1$H-NMR (CDCl$_3$): δ (ppm) 7.45 (d, 2H); 7.2 (d, 1H); 7.0 (bs, 2H); 6.75 (m, 2H); 4.65 (bm, 2H); 4.4–4.15 (bq, 2H); 4.05 (bm, 1H); 3.9 (bm, 1H); 3.45 (bm, 2H); 3,25 (bt, 1H); 3.05 (s, 3H); 1.45 (s, 9H).

Intermediate 59

3-[(3,5-Bis-trifluoromethyl-benzyl)-methylcarbamoyl]-4-(4-trifinoromethyl-phenyl)-piperazine-1-carboxylic acid tert-butyl ester DIPEA (84 μL) and O-(benzotriazol-1-yl)-N,N,N'N'-tetramethyluronium tetrafluoroborate (67 mg) were added to a solution of intermediate 57 (60 mg) in anhydrous DMF (7 mL) under a Nitrogen atmosphere. After stirring for 1 hour, 3,5-(bis-trifluoromethyl)-benzyl-methylamine hydrochloride (52 mg) was added and the mixture was stirred at r.t for 20 hours. The solution was partitioned between AcOEt and water. The organic extracts was washed with brine, dried and concentrated in vacuo to a crude, which was purified by flash chromatography (CH/AcOEt 7:3) to give the title compound (70 mg).

$^1$H-NMR (CDCl$_3$): δ (ppm) 7.75 (s, 1H); 7.6 (bm, 2H); 7.45 (d, 2H); 6.75 (m, 2H); 4.85 (bm, 1H); 4.75 (bm, 2H); 4.5–4.2 (bm, 2H); 4.05 (bm, 1H); 3.6 (bm, 1H); 3,25 (bt, 1H); 3.1 (s, 3H); 1.45 (s, 9H). MS (ES/+): m/z=636 [M+Na]$^+$.

Intermediate 60

2(4-Fluoro-2-methyl-phenylamino)-ethanol hydrochloride

In a glass round bottom flask 4-fluoro-2-methylaniline (1 g), 2-chloroethanol (0.64 mL) and DIPEA (1.67 mL) were added. The homogeneous mixture was heated to 125–130° C. for 6–10 hours. Then it was cooled to 60° C. and it was diluted with AcOEt (7 mL). The mixture was cooled to 15–20° C. and left overnight without stirring.

The following day, stirring the mixture at 20° C., a solution of 6N hydrochloric acid solution in isopropanol (2.5 mL) was dropped over 20 minutes. After a while a solid precipitates and it was stirred for 2 hours at 20° C. Then it was filtered and washed with AcOEt (3.5 mL) and dried at 40° C. for 18 hours to give the title compound as a white solid (1.07 g).

$^1$H-NMR ($d_6$-DMSO): δ (ppm) 11.0–7.0 (bs, 2–3H); 7.41 (bm, 1H); 7.18 (dd, 1H);7.12 (dt, 1H); 3.68 (t, 2H); 3.25 (t, 2H); 2.38 (s, 3H).

Intermediate 61

3',5'-Dichloroacetophenone

A solution of methyl iodide (4 mL) in anhydrous Et2O (40 mL) was dropped into a suspension of magnesium (1.6 g) in anhydrous Et2O (16 mL) under a Nitrogen atmosphere. At the end of the dropping, benzene (120 mL) was added and the Et2O eliminated with a Nitrogen flux. Then, a solution of 3,5-dichlorobenzonitrile (4 g) in benzene (48 mL) was added and the mixture was heated to reflux for 3 hours. The solution was cooled to 0° C. and a 6N hydrochloric acid solution was added and the mixture was stirred overnight at r.t. Water and Et2O were added and the layers were separated. The organic phase was washed with a saturated sodium hydrogen carbonate solution and brine, dried and concentrated in vacuo. The residue was purified by flash chromatography (CH/AcOEt 95:5) to give the title compound (2.55 g) as an orange oil.

T.l.c.: CH/AcOEt 8:2, Rf=0.64. NMR (CDCl$_3$): δ (ppm) 7.75 (s, 2H); 7.6 (s, 1H); 2.55 (s, 3H).

Intermediate 62

[1-(3,5-Dichloro-phenyl)-ethyl]-methylamine

Methylamine (2M solution in MeOH—13 mL) was added to a solution of intermediate 61 (500 mg) in MeOH (26 mL) under a Nitrogen atmosphere. The mixture was stirred at r.t. for 18 hours, then it was cooled to 0° C. and sodium borohydride (98 mg) was added. The mixture was stirred at 0° C. for 2 hours, then it was quenched with water and extracted with DCM. The organic layer was dried and concentrated in vacuo to give the title compound (340 mg) as yellow oil.

T.l.c.: CH/AcOEt 1:1, Rf=0.15. NMR (CDCl$_3$): δ (ppm) 7.3 (m, 3H); 3.6 (q, 1H); 2.3 (s, 3H); 1.35 (d, 3H). MS (ES/+): m/z=204 [M+H]$^+$.

EXAMPLE 1

(+/−) 1-(4-Fluoro-2-methyl-phenyl)-piperazine-2-carboxylic acid (3.5-bis-trifluoromethyl-benzyl) methylamide hydrochloride A mixture of intermediate 5 (0.7 g) in EtOH (85 mL) containing glacial acetic acid (0.28 mL) and 10% palladium on carbon (0.155 g) was stirred under hydrogen at 70 p.s.i. for 22 hours. The mixture was filtered through a pad of celite and the pad washed with further EtOH (50 mL). Concentration in vacuo gave a crude which was purified by flash chromatography (DCM/EtOH/NH$_4$OH from 100:8:1 to 75:8:1 to give 1-(4-fluoro-2-methyl-phenyl)-piperazine-2-carboxylic acid (3,5-bis-trifluoromethyl-benzyl)-methylamide (0.5 g) as a yellow gum (T.l.c.: AcOEt/MeOH 8:2, Rf=0.18).

This material (91 mg) was dissolved in anhydrous Et2O (1.5 mL) and treated at 0° C. with hydrochloric acid (1M in Et2O—0.25 mL). The mixture was stirred at 0° C. for 15 minutes, then concentrated in vacuo. The residue was washed with pentane (2×4 mL) to give the title compound (90 mg) as a whitish solid.

M.p.: 85–90° C. IR (film, cm$^{-1}$): 3404 (NH), 1641 (C=O). $^1$H-NMR (d$_6$-DMSO): δ (ppm) 7.89 (s, 1H); 7.54 (s, 2H); 7.09 (dd, 1H); 6.88 (dd, 1H); 6.72 (td, 1H); 4.7–4.5 (m, 1H); 4.4–4.2 (m, 2H); 3.04 (s, 3H); 2.82 (bd, 1H); 2.6 (m, 3H); 2.28 (m, 2H); 2.23 (s, 3H); 2.2 (s, 3H). MS (ES/+): m/z=478 [M-HCl+H]$^+$.

EXAMPLE 2

(+/−)-1-(4-Fluoro-2-methyl-phenyl)-piperazine-2-carboxylic acid (3,5-dichloro-benzyl)-methylamide hydrochloride Method A:

TFA (1.5 mL) was dropped into a solution of intermediate 9 (65 mg) in dry DCM (5 mL) previously cooled to 0° C. under a Nitrogen atmosphere. The solution was stirred at 0° C. for 2.5 hours, then concentrated in vacuo. The residue was purified by flash chromatography (DCM/MeOH 95:5) to give 1-(4-fluoro-2-methyl-phenyl)-piperazine-2-carboxylic acid (3,5-dichloro-benzyl)-methylamide (25 mg) as a colourless oil.

T.l.c.: DCM/MeOH 9:1, Rf=0.2.

This material (25 mg) was dissolved in anhydrous Et2O (2 mL) and treated at 0° C. with hydrochloric acid (1M in Et2O—73 □L). The mixture was stirred at 0° C. for 30 minutes, then concentrated in vacuo. The residue was washed with pentane to give the title compound (15 mg) as an off-white solid.

$^1$H-NMR (d$_6$-DMSO): δ (ppm) 9.21 (bs, 1H); 8.62 (bs, 1H); 7.44 (bs, 1H); 7.05 (m, 3H); 6.88 (m, 2H); 4.61 (d, 1H); 4.55 (bt, 1H); 4.19 (d, 1H); 3.7–2.97 (bm, 6H); 2.67 (s, 3H); 2.33 (s, 3H). MS (ES/+): m/z=410 [M+H—HCl]$^+$.

Method B

The compound of Example 2a (700 mg) was dissolved in anhydrous Et2O (15 mL) and treated at 0° C. with hydrochloric acid (1M in Et2O—1.87 mL). The mixture was stirred at 0° C. for 30 minutes, then concentrated in vacuo. The residue was triturated with pentane (3×5 mL) to give the title compound (735 mg) as an off-white solid.

M.p.: 110–113° C. $^1$H-NMR (d$_6$-DMSO): δ (ppm) 9.21 (bs, 1H); 8.62 (bs, 1H); 7.44 (bs, 1H); 7.05 (m, 3H); 6.88 (m, 2H); 4.61 (d, 1H); 4.55 (bt, 1H); 4.19 (d, 1H); 3.7–2.97 (bm, 6H); 2.67 (s, 3H); 2.33 (s, 3H).

EXAMPLE 2a (+/−) 1-(4-Fluoro-2-methyl-phenyl)-piperazine-2-carboxylic acid, (3,5-dichloro-benzyl)-methylamide Method A TFA (20 mL) was dropped into a solution of intermediate 9 (3.14 g) in dry DCM (80 mL) previously cooled to 0° C. under a Nitrogen atmosphere. The solution was stirred at 0° C. for 5 hours, then concentrated in vacuo. The residue was diluted with AcOEt (100 mL) and washed with a saturated sodium carbonate solution (4×60 mL) and brine (50 mL). The organic layer was concentrated in vacuo. The residue was triturated with Et2O (2×10 mL) to give the title compound (2.1 g) as a white solid. Concentration in vacuo of the organic phase followed by purification of the residue by flash chromatography (DCM/MeOH 95:5) gave a further amount (82 mg) of the title compound.

Method B

DIPEA (0.48 mL) was added to the solution of intermediate 9a in AcOEt (6 mL) at room temperature. To the mixture 1-chloroethyl chloroformate (0.44 mL) was dropped over 15 minutes. The resulting solution was stirred at room temperature over 2 hours then 1N hydrochloric acid (5.5 mL) was added and the reaction was heated at 60° C. for 2 hours. The organic mixture was cooled to room temperature then isooctane (10 mL) and MeOH (2 mL) were added.

The the two phases were separated and the aqueous one was washed again with isooctane/AcOEt 2/1(8 mL).

To the aqueous layer AcOEt (10 mL) was added and under a vigorous stirring a 10% ammonium hydroxide solution (6 mL) was dropped. The pH of the solution was check (it should be more than 8) The two phases were separated and the organic layer was washed with water (2×5 mL). The organic layer was concentrated to 7 vol and then diluted again with AcOEt (7 mL) and finally concentrated to 7 mL. The solid was then precipitated by isooctane (7 mL) addition. The solid was stirred overnight at room temperature. It was filtered and washed with a 1/1 isooctane/AcOEt mixture (3 mL).After drying into an oven at 40° C., the title compound (0.47 g) was obtained.

T.l.c.: DCM/MeOH 9:1, Rf=0.2. M.p.: 161–2° C. $^1$H-NMR (d$_6$-DMSO): δ (ppm) 7.4 (s, 1H); 7.08 (m, 1H); 6.97 (m, 1H); 6.83 (m, 1H); 6.82 (s, 2H); 4.75 (d, 1H); 4.6–3.96 (m, 2H); 3.1–2.7 (m, 2H); 2.67 (s, 3H); 2.8–2.2 (m, 3H).

EXAMPLE 3

(+)-1-(4-Fluoro-2-methyl-phenyl)-piperazine-2-carboxylic acid (3,5-dichloro-benzyl)-methylamide hydrochloride Method A TFA (0.8 mL) was dropped into a solution of intermediate 13 (167 mg) in dry DCM (4 mL) previously cooled to 0° C. under a Nitrogen atmosphere. The solution was stirred at 0° C. for 3 hours, then concentrated in vacuo. The residue was dissolved in AcOEt and washed with 10% sodium carbonate solution, dried and concentrated in vacuo. The residue was purified by flash chromatography (DCM/MeOH 9:1) to give (+)-1-(4-fluoro-2-methyl-phenyl)-piperazine-2-carboxylic acid (3,5-dichloro-benzyl)-methylamide (120 mg) as a white solid (T.l.c.: DCM/MeOH 9:1, Rf=0.2).

This material (120 mg) was dissolved in anhydrous Et2O (3 mL) and treated at −5° C. with hydrochloric acid (1M in Et2O—0.33 mL). The mixture was stirred at −5° C. for 30 minutes, then concentrated in vacuo. The residue was washed with pentane to give the title compound (122 mg) as a white solid.

SFC: column Chirapack AD 25 cm×4.6 mm, column temperature 35° C., mobile phase CO2/EtOH (+0.15 iso-propanol) 65:35, flow 2.5 mL/min, column pressure 180 bar; detector UV-MS, λ=225 nm; retention time 2.28 minutes m/z=410 [M+H]$^+$, 87% a/a).

Method B

The compound of Example 5a (233 mg) was dissolved in anhydrous Et2O (10 mL) and treated at 0° C. with hydrochloric acid (1M in Et2O—0.62 mL). The mixture was stirred at 0° C. for 30 minutes, then concentrated in vacuo. The residue was washed with pentane (3×2 mL) to give the title compound (249 mg) as an off-white solid.

$^1$H-NMR (d$_6$-DMSO): δ (ppm) 9.21 (bs, 1H); 8.62 (bs, 1H); 7.44 (bs, 1H); 7.05 (m, 3H); 6.88 (m, 2H); 4.61 (d, 1H); 4.55 (bt, 1H); 4.19 (d, 1H); 3.7–2.97 (bm, 6H); 2.67 (s, 3H); 2.33 (s, 3H). MS (ES/+): m/z=410 [M+H—HCl]$^+$. [α]$_D$=+ 25.3 (c=0.49% w/v in DMSO)

EXAMPLE 4

(−)-1-(4-Fluoro-2-methyl-phenyl)-piperazine-2-carboxylic acid (3,5-dichloro-benzyl)-methylamide hydrochloride (enantiomer 2)

Method A

TFA (1 mL) was dropped into a solution of intermediate 16 (170 mg) in dry DCM (5 mL) previously cooled to 0° C. under a Nitrogen atmosphere. The solution was stirred at 0° C. for 2 hours, then concentrated in vacuo. The residue was dissolved in AcOEt (20 mL) and washed with water (5 mL) and a saturated solution of potassium carbonate (10 mL). The organic layer was dried and concentrated in vacuo. The residue was purified by flash chromatography (DCM/MeOH 9:1) to give (−)-1-(4-fluoro-2-methyl-phenyl)-piperazine-2-carboxylic acid (3,5-dichloro-benzyl)-methylamide (120 mg) as a white solid (T.l.c.: DCM/MeOH 9:1, Rf=0.2).

This material (120 mg) was dissolved in anhydrous Et2O (5 mL) and AcOEt (1 mL) and treated at −5° C. with hydrochloric acid (1M in Et2O—0.323 mL). The mixture was stirred at −5° C. for 30 minutes, then concentrated in vacuo. The residue was washed with pentane (3×2 mL) to give the title compound (115 mg) as a white solid.

SFC: column Chirapack AD 25 cm×4.6 mm, column temperature 35° C., mobile phase CO2/EtOH (+0.15 iso-propanol) 65:35, flow 2.5 mL/min, column pressure 180 bar; detector UV-MS, λ=225 nm; retention time 4.61 minutes; 82% a/a).

Method B

The compound of Example 5b (192 mg) was dissolved in anhydrous Et2O (10 mL) and treated at 0° C. with hydrochloric acid (1M in Et2O—0.515 mL). The mixture was stirred at 0° C. for 30 minutes, then concentrated in vacuo. The residue was washed with pentane (2×2 mL) to give the title compound (200 mg) as an off-white solid.

$^1$H-NMR (d$_6$-DMSO): δ (ppm) 9.35 (bs, 1H); 8.7 (bs, 1H); 7.42 (s, 1H); 7.04 (s, 2H); 7.1–6.8 (m, 3H); 4.6 (d, 1H); 4.57 (m, 1H); 4.16 (d, 1H); 3.6–2.98 (bm, 6H); 2.68 (s, 3H); 2.31 (s, 3H). MS (ES/+): m/z=410 [M+H—HCl]$^+$. [α]$_D$=− 4.6 (c=0.52% w/v in DMSO—not clear solution)

EXAMPLE 4a

Example 3 and example 4 as 75:25 mixture

Example 3 (75.5 mg) and example 4 (25.6 mg) were mixed to give enriched mixtures 75:25 to give the title compound.

HPLC: column Chirapack AD 25 cm×4.6 mm×5 µm, mobile phase n-hexane/EtOH 80:20, flow 7 ml/min; detector DAD, λ=220–360 nm, scan range 150–1000; ionisation method ES/+; retention time 6.72 minutes (enantiomer 1; 75.6% a/a) and 8.91 minutes (enantiomer 2; 24.4% a/a).

EXAMPLE 4b

Example 3 and example 4 as 25:75 mixture

Example 3(25.2 mg) and Example 4(75.2 mg) were mixed to give enriched mixtures 75:25 to give the title compound.

HPLC: column Chiralpack AD 25 cm×4.6 mm×5 µm, mobile phase n-hexane/EtOH 80:20, flow 7 ml/min; detector DAD, λ=220–360 nm, scan range 150–1000; ionisation method ES/+; retention time 6.66 minutes (enantiomer 1; 26.4% a/a) and 8.82 minutes (enantiomer 2; 73.6% a/a).

EXAMPLE 5

1-(4-Fluoro-2-methyl-phenyl)-piperazine-2-carboxylic acid, (3,5-dichloro-benzyl)-methylamide (enantiomer 1) (5a)

1-(4-Fluoro-2-methyl-phenyl)-piperazine-2-carboxylic acid (3,5-dichloro-benzyl)-methylamide (enantiomer 2) (5b)

The compound of Example 2a (500 mg) was separated by HPLC (conditions: column Chiralpack AD 25 cm×2 mm, mobile phase n-hexane/EtOH 80:20, flow 7 mL/min; detector DAD, λ=310 nm) into enantiomers. Thus, the title compound 5a (233 mg) and the title compound 5b (192 mg) were obtained.

EXAMPLE 5a

HPLC-MS: column Phenomenex LUNA C18 15 cm×4.6 mm×5 µm, mobile phase buffer ammonium acetate 10 mM pH=6.8/acetonitrile from 70:30 to 10:90 in 10 minutes, then 10:90 for 5 minutes; detector DAD, MS, ELSD, λ=220–360 nm; ionisation method ES/+, scan range 150–1000; retention time 11.94 minutes, m/z=410 [M+H]$^+$.

EXAMPLE 5b

HPLC-MS: column Phenomenex LUNA C18 15 cm×4.6 mm×5 µm, mobile phase buffer ammonium acetate 10 mM pH=6.8/acetonitrile from 70:30 to 10:90 in 10 minutes, then 10:90 for 5 minutes; detector DAD, MS, ELSD, λ=220–360 nm; ionisation method ES/+, scan range 150–1000; retention time 10.66 minutes, m/z=410 [M+H]$^+$.

EXAMPLE 6a 1-(4-Fluoro-2-methyl-phenyl)-piperazine-2-carboxylic acid [1-(3,5-dichloro-phenyl)-ethyl]-methylamide (diastereoisomer A TFA (0.6 mL) was added to a solution of intermediate 8a (33 mg) in anhydrous DCM (3 mL) previously cooled to 0° C. under a Nitrogen atmosphere. The solution was stirred at 0° C. for 5 hours, then it was concentrated in vacuo. The residue was diluted with AcOEt (10 mL) and washed with a saturated sodium carbonate solution (3×5 mL) and brine (5 mL). The organic layer was dried and concentrated in vacuo to a residue which was purified by flash chromatography (from DCM 100% to DCM/MeOH 95:5) to give the title compound (10.7 mg) as a yellow wax.

T.l.c.: DCM/MeOH 9:1, Rf=0.57. IR (nujol, cm$^{-1}$): 1629 (C=O). $^1$H-NMR (d$_6$-DMSO—70° C.): δ (ppm) 7.39 (bs, 1H); 7.06 (dd, 1H); 6.95 (bs, 2H); 7.0–6.8 (bm, 2H); 5.49 (bq, 1H); 4.09 (bd, 1H); 3.2–2.5 (bm, 9H); 2.29 (s, 3H); 1.25 (bm, 3H). MS (ES/+): m/z=424 [M+H]$^+$.

EXAMPLE 6b 1-(4-Fluoro-2-methyl-phenyl)-piperazine-2-carboxylic acid [1-(3,5-dichloro-phenyl)-ethyl]-methylamide (6b) (diastereoisomer B)

TFA (0.6 mL) was added to a solution of intermediate 8b (28 mg) in anhydrous DCM (3 mL) previously cooled to 0° C. under a Nitrogen atmosphere. The solution was stirred at 0° C. for 5 hours, then it was concentrated in vacuo. The residue was diluted with AcOEt (10 mL) and washed with a saturated sodium carbonate solution (3×5 mL) and brine (5 mL). The organic layer was dried and concentrated in vacuo to a residue which was purified by flash chromatography (from DCM 100% to DCM/MeOH 95:5) to give the title compound (16 mg) as a yellow wax.

T.l.c.: DCM/MeOH 9:1, Rf=0.50. (nujol, cm$^{-1}$): 1640 (C=O). $^1$H-NMR (d$_6$-DMSO—70° C.): δ (ppm) 7.46 (t, 1H); 7.06 (dd, 1H); 6.99 (dd, 1H); 6.88 (bs, 2H); 6.84 (dt, 1H); 5.56 (q, 1H); 4.17 (bd, 1H); 3.2–3.0 (m, 2H); 3.0–2.8 (m, 3H); 2.6 (bm, 1H); 2.62 (s, 3H); 2.3 (s, 3H); 1.3 (d, 3H). MS (ES/+): m/z=424 [M+H]$^+$.

EXAMPLE 7

1-(4-Fluoro-2-methyl-phenyl)-piperazine-2-carboxylic acid [1-(3,5-dichloro-phenyl)-ethyl]-methylamide (7a) (diastereoisomer 1)

1-(4-Fluoro-2-methyl-phenyl)-piperazine-2-carboxylic acid [1-(3,5-dichloro-phenyl)-ethyl]-methylamide (7b) (diastereoisomer 2)

The compound of Example 6b (12 mg) was separated by HPLC (conditions: column Chiralpack AD 25 cm×2 mm, mobile phase n-hexane/EtOH 80:20, flow 7 mL/min; detector DAD, λ=225 nm) into enantiomers. Thus, the title compound 7a (4 mg) and the title compound 7b (4.2 mg) were obtained.

Compound 7a:
HPLC: column Chiralpack AD 25 cm×4.6 mm×5 μm, mobile phase n-hexane/EtOH 80:20; flux=1 mL/min; retention time 6.5 minutes.

Compound 7b:
HPLC: column Chiralpack AD 25 cm×4.6 mm×5 μm, mobile phase n-hexane/EtOH 80:20; flux=1 mL/min; retention time 7.9 minutes.

EXAMPLE 8

1-(4-Fluoro-2-methyl-phenyl)-piperazine-2-carboxylic acid (3,5bis-trifluoromethyl-benzyl)-methylamide hydrochloride (enantiomer 1)

A mixture of intermediate 18 (54 mg) in EtOH (10 mL) containing glacial acetic acid (90 μL) and 10% palladium on carbon (18 g) was stirred under hydrogen at 6 atmospheres for 3 hours. The mixture was filtered through a pad of celite, which was washed with further EtOH. Concentration in vacuo gave a crude which was purified by flash chromatography (DCM/MeOH 95:5) to give 1-(4-fluoro-2-methyl-phenyl)-piperazine-2-carboxylic acid (3,5-bis-trifluoromethyl-benzyl)-methylamide (38 mg) as a yellow gum (T.l.c.: AcOEt/MeOH 8:2, Rf=0.18).

This material (38 mg) was dissolved in anhydrous Et2O (2 mL) and treated at 0° C. with hydrochloric acid (1M in Et2O —87 μL). The mixture was stirred at 0° C. for 30 minutes, then concentrated in vacuo. The residue was washed with pentane to give the title compound (11 mg) as a whitish solid.

$^1$H-NMR (d$_6$-DMSO-60° C.): δ (ppm) 9.0 (bs, 1H); 8.5 (bs, 1H); 7.97 (s, 1H); 7.78 (s, 2H); 6.98 (dd, 1H); 6.92 (dd, 1H); 6.72 (dt, 1H); 4.78 (d, 1H); 4.5 (t, 1H); 4.35 (d, 1H); 3.44–2.93 (m, 6H); 2.65 (s, 3H); 2.29 (s, 3H).

SFC: column Chirapack AD 25 cm×4.6 mm, column temperature 35° C., mobile phase CO2/EtOH (+0.15 isopropanol) 65:35, column pressure 180 bar, flow 2.5 mL/min, detector UV-MS, λ=225 nm; retention time 2.72 minutes (enantiomer 1); m/z=78 [M+H—HCl]$^+$, 73% a/a).

EXAMPLE 9

1-(4-Fluoro-2-methyl-phenyl)-piperazine-2-carboxylic acid (3,5-bis-trifluoromethyl-benzyl)-methylamide hydrochloride (enantiomer 2)

A mixture of intermediate 20 (90 mg) in EtOH (10 mL) containing glacial acetic acid (0.1 mL) and 10% palladium on carbon (30 g) was stirred under hydrogen at 6 atmospheres for 3 hours. The mixture was filtered through a pad of celite, which was washed with further EtOH. Concentration in vacuo gave a crude which was purified by flash chromatography (DCM/MeOH 95:5) to give 1-(4-fluoro-2-methyl-phenyl)-piperazine-2-carboxylic acid (3,5-bis-trifluoromethyl-benzyl)-methylamide (36 mg) as a yellow gum T.l.c.: AcOEt/MeOH 8:2, Rf=0.18).

This material (36 mg) was dissolved in anhydrous Et2O (2 mL) and treated at 0° C. with hydrochloric acid (1M in Et2O—83 μL). The mixture was stirred at 0° C. for 30 minutes, then concentrated in vacuo. The residue was washed with pentane to give the title compound (27 mg) as a whitish solid.

$^1$H-NMR (d$_6$-DMSO): δ (ppm) 9.19 (bs, 1H); 8.58 (bs, 1H); 7.97 (s, 1H); 7.77 (s, 2H); 7.0–6.8 (m, 2H); 6.73 (dt, 1H); 4.78 (d, 1H); 4.54 (t, 1H); 4.34 (d, 1H); 3.43 (bs, 3H); 3.4–3.15 (m, 3H); 2.94 (m, 1H); 2.68 (s, 3H); 2.29 (s, 3H).

SFC: column Chirapack AD 25 cm×4.6 mm, column temperature 35° C., mobile phase CO2/EtOH (+0.15 isopropanol) 65:35, column pressure 180 bar; flow 2.5 mL/min, detector UV-MS, λ=225 nm; retention time 3.6 minutes (enantiomer 2; m/z=478 [M+H—HCl]+, 79% a/a).

EXAMPLE 10

(+/−) 1-(4-Fluoro-2-methyl-phenyl)-piperazine-2-carboxylic acid (3,5-dibromo-benzyl)-methylamide hydrochloride TFA (1.72 mL) was dropped into a solution of intermediate 21 (316 mg) in dry DCM (6.6 mL) previously cooled to 0° C. under a Nitrogen atmosphere. The solution was stirred at 0° C. for 5 hours, then concentrated in vacuo. The residue was diluted with AcOEt and washed with a saturated sodium hydrogen carbonate solution. The organic layer was dried and concentrated in vacuo. The residue was purified by flash chromatography (DCM/MeOH 9:1) to give 1-(4-fluoro-2-methyl-phenyl)-piperazine-2-carboxylic acid (3,5-dibromo-benzyl)-methylamide (149.4 mg) as a colourless oil.

T.l.c.: DCM/MeOH 9:1, Rf=0.34.

This material (149.4 mg) was dissolved in anhydrous Et2O (3.3 mL) and treated at −10° C. with hydrochloric acid (1M in Et2O—0.36 mL). The mixture was stirred at −10° C. for 30 minutes, then concentrated in vacuo. The residue was washed with pentane to give the title compound (141 mg) as a white solid.

$^1$H-NMR (d$_6$-DMSO): δ (ppm) 8.8 (bs, 2H); 7.73 (bs, 1H); 7.27 (bs, 2H); 7.04 (dd, 1H); 6.99 (m, 1H); 6.88 (m, 1H); 4.7–4.0 (bm, 3H); 3.5–2.8 (bm, 6H); 2.59 (s, 3H); 2.3 (s, 3H). MS (ES/+): m/z=498 [M+H—HCl]$^+$.

EXAMPLE 11

(+/−) 1-(4-Fluoro-2-methyl-phenyl)-piperazine-2-carboxylic acid (3,4-dibromo-benzyl)-methylamide hydrochloride TFA (0.52 nm) was dropped into a solution of intermediate 22 (94.1 mg) in dry DCM (2 mL) previously cooled to 0° C. under a Nitrogen atmosphere. The solution was stirred at 0° C. for 5 hours, then concentrated in vacuo. The residue was diluted with AcOEt (2 mL) and washed with a saturated sodium hydrogen carbonate solution. The organic layer was dried and concentrated in vacuo. The reaction was not complete, thus the residue was dissolved in anhydrous DCM (1.3 mL), cooled to 0° C. under a Nitrogen atmosphere and treated with TFA (0.34 mL). The solution was stirred at 0° C. for 5 hours, then concentrated in vacuo. The residue was diluted with AcOEt (2 mL) and washed with a saturated sodium hydrogen carbonate solution. The organic layer was dried and concentrated in vacuo. The residue was purified by flash chromatography (DCM/MeOH 9:1) to give 1-(4-fluoro-2-methyl-phenyl)-piperazine-2-carboxylic acid (3,4-dibromo-benzyl)-methylamide (41.8 mg) as a colourless oil.

T.l.c.: DCM/MeOH 8:2, Rf=0.6.

This material (41.8 mg) was dissolved in anhydrous Et2O (0.92 mL) and treated at −10° C. with hydrochloric acid (1M in Et2O—0.1 mL). The mixture was stirred at −10° C. for 30 minutes, then concentrated in vacuo. The residue was washed twice with pentane to give the title compound (10.5 mg) as a white solid.

$^1$H-NMR (d$_6$-DMSO): δ (ppm) 9.1–8.55 (2bs, 2H); 7.62 (d, 1H); 7.45 (bs, 1H); 7.05 (dd, 1H); 6.99 (m, 1H); 6.87 (m, 2H); 4.7–4.0 (m, 3H); 3.5–2.8 (bm, 6H); 2.56 (bs, 3H); 2.3 (s, 3H).

EXAMPLE 12

1-(4-Fluoro-2-methyl-phenyl)-piperazine-2-carboxylic acid (3,5-dibromo-benzyl)-methylamide hydrochloride (12a—enantiomer 1)

1-(4-Fluoro-2-methyl-phenyl)-piperazine-2-carboxylic acid (3.5-dibromo-benzyl)-methylamide hydrochloride (12b—enantiomer 2)

The compound of EXAMPLE 10 (120 mg) was dissolved in a 5% sodium hydrogen carbonate solution (10 mL) and extracted with AcOEt (15 mL). The organic layer was dried and concentrated in vacuo to give 1-(4-fluoro-2-methyl-phenyl)-piperazine-2-carboxylic acid (3,5-dibromo-benzyl)-methylamide (94 mg). This material was separated into enantiomers by HPLC (conditions: column Chiralcel OD 25 cm×20 mm, mobile phase n-hexane/EtOH 80:20, flow 7 mL/min; detector DAD, λ=225 nm). Thus, 1-(4-fluoro-2-methyl-phenyl)-piperazine-2-carboxylic acid (3,5-dibromo-benzyl)-methylamide was obtained as:

enantiomer 1 (36.4 mg): retention time 20.8 minutes enantiomer 2 (37.8 mg): retention time 26 minutes.

EXAMPLE 12a

Enantiomer 1 (36.4 mg) was dissolved in anhydrous Et2O (1 mL) and treated at −10° C. with hydrochloric acid (1M in Et2O—87.5 μL). The mixture was stirred at 0° C. for 15 minutes, then concentrated in vacuo. The residue was triturated with pentane (2×1 mL) to give the title compound 12a (26.2 mg) as a white solid.

HPLC-MS: column Chiralcel OD 25 cm×4.6 mm, mobile phase n-hexane/EtOH 80:20; flow 1 ml/min; detector DAD, λ=225 nm; retention time 7.3 minutes (100% a/a).

M.p.: 79–80° C. (dec.). $^1$H-NMR (d$_6$-DMSO—60° C.): δ (ppm) 9.3–8.62 (2s, 2H); 7.68 (s, 1H); 7.26 (s, 2H); 7.0 (m, 2H); 6.87 (m, 1H); 4.6 (d, 1H); 4.54 (m, 1H); 4.15 (d, 1H); 3.45–3.3 (m, 2H); 3.45–3.3 (m, 2H); 3.2–3.0 (m, 2H); 2.64 (s, 3H); 2.31 (s, 3H).

EXAMPLE 12b

Enantiomer 2 (37.8 mg) was dissolved in anhydrous Et2O (1 mL) and treated at 0° C. with hydrochloric acid (1M in Et2O—90.8 μL). The mixture was stirred at 0° C. for 15 minutes, then concentrated in vacuo. The residue was triturated with pentane (2×1 mL) to give the title compound 12b (28.1 mg) as a white solid.

HPLC-MS: column Chiralcel OD 25 cm×4.6 mm, mobile phase n-hexane/EtOH 80:20; flow 1 mL/min; detector DAD, λ=225 nm; retention time 8.9 minutes (100% a/a).

M.p.:79–80° C. (dec.). $^1$H-NMR (d$_6$-DMSO—70° C.): δ (ppm) 8.4–8.1 (bs, 2H); 7.68 (s, 1H); 7.25 (s, 2H); 7.0 (m, 2H); 6.87 (m, 1H); 4.6–4.18 (2d, 2H); 4.44 (m, 1H); 3.39 (m, 2H); 3.26 (m, 2H); 3.1–2.9 (m, 2H); 2.66 (s, 3H); 2.35 (s, 3H).

EXAMPLE 13

1-(4-Fluoro-2-methyl-phenyl)-piperazine-2-carboxylic acid [1-(R)-(3,5-bis-trifluoromethyl-phenyl)-ethyl]-methylamide (diastereoisomer 1)

TFA (0.5 mL) was added to a solution of intermediate 23a (12 mg) in anhydrous DCM (2 mL) previously cooled to 0° C. under a Nitrogen atmosphere. The solution was stirred at 0° C. for 3 hours, then it was concentrated in vacuo. The residue was diluted with a saturated sodium carbonate solution and extracted twice with AcOEt. The organic layer was dried and concentrated in vacuo to a residue which was purified by flash chromatography (DCM/MeOH 95:5) to give the title compound (5 mg) as a colourless oil.

$^1$H-NMR (d$_6$-DMSO—50° C.): δ (ppm) 7.8 (bs, 1H); 7.56 (bs, 2H); 6.93 (bm, 1H); 6.86 (bd, 1H); 6.67 (bm, 1H); 5.99 (bq, 1H); 4.14 (t, 1H); 3.62 (bm, 3H); 3.45–3.1 (m, 2H); 2.82 (bm, 1H); 2.42 (s, 3H); 2.33 (s, 3H); 2.07 (s, 3H); 1.45 (bd, 3H). MS (ES/+): m/z=492 [M+H]$^+$.

EXAMPLE 14

1-(4-Fluoro-2-methyl-phenyl)-piperazine-2-carboxylic acid [1-(R)-(3,5-bis-trifluoromethyl-phenyl)-ethyl]-methylamide trifluoroacetate (diastereoisomer 2)

TFA (1 mL) was added to a solution of intermediate 23b (12 mg) in anhydrous DCM (3 mL) previously cooled to 0° C. under a Nitrogen atmosphere. The solution was stirred at 0° C. for 20 hours, then it was concentrated in vacuo. The residue was diluted with a saturated sodium carbonate solution and extracted twice with AcOEt. The organic layer was dried and concentrated in vacuo to a residue which was purified by flash chromatography (DCM/MeOH 95:5) to give the title compound (12 mg) as a colourless oil.

$^1$H-NMR (d$_6$-DMSO—50° C.): δ (ppm) 7.76 (bs, 1H); 7.51 (bs, 2H); 7.09 (m, 1H); 6.9–6.8 (m, 2H); 5.94 (m, 1H); 4.03 (m, 1H); 3.4 (m, 1H); 3.3 (m, 1H); 3.2 (m, 1H); 3.14 (m, 1H); 3.0 (m, 1H); 2.6 (m, 1H); 2.54 (s, 3H); 2.35 (s, 3H); 1.35 (d, 3H). MS (ES/+): m/z=492 [M+H]$^+$.

EXAMPLE 15

(+/−) 1-(4-Fluoro-2-methyl-phenyl)-piperazine-2-carboxylic acid (3-chloro-4-fluoro-benzyl)methylamide hydrochloride TFA (1.25 mL) was added to a solution of intermediate 24 (43 mg) in anhydrous DCM (4 mL) previously cooled to 0° C. under a Nitrogen atmosphere. The solution was stirred at 0° C. for 20 hours, then it was concentrated in vacuo. The residue wag diluted with a saturated sodium carbonate solution and extracted twice with AcOEt. The organic layer was dried and concentrated in vacuo to a residue which was purified by flash chromatography (DCM/MeOH 95:5) to give 1-(4-fluoro-2-methyl-phenyl)-piperazine-2-carboxylic acid (3-chloro-4-fluoro-benzyl)methylamide (27 mg).

This material (27 mg) was dissolved in anhydrous Et2O (2 mL) and treated at 0° C. with hydrochloric acid (1M in Et2O—82 μL). The mixture was stirred at 0° C. for 30 minutes, then concentrated in vacuo. The residue was triturated with pentane to give the title compound (18.3 mg) as a white solid.

$^1$H-NMR (d$_6$-DMSO—70° C.): δ (ppm) 9.8–8.5 (b, 2H); 7.2 (m, 2H); 7.01 (m, 2H); 6.86 (m, 1H); 4.58 (bd, 1H); 4.5 (bm, 1H); 4.14 (d, 1H); 3.6–2.9 (m, 6H); 2.67 (s, 3H); 2.31 (s, 3H). MS (ES/+): m/z=394 [M+H—HCl]$^+$.

EXAMPLE 16

(+/−) 1-(4-Fluoro-2-methyl-phenyl)-piperazine-2-carboxylic acid (2,5-dichloro-benzyl)-methylamide hydrochloride TFA (1.5 mL) was added to a solution of intermediate 25 (50 mg) in anhydrous DCM (5 mL) previously cooled to 0° C. under a Nitrogen atmosphere. The solution was stirred at 0° C. overnight, then it was concentrated in vacuo. The residue was diluted with a saturated sodium carbonate solution and extracted twice with AcOEt. The organic layer was dried and concentrated in vacuo to a residue which was purified by flash chromatography (DCM/MeOH 95:5) to give 1-(4-fluoro-2-methyl-phenyl)-piperazine-2-carboxylic acid (2,5dichloro-benzyl)-methylamide (22 mg).

This material (22 mg) was dissolved in anhydrous Et2O (2 mL) and treated at 0° C. with hydrochloric acid (1M in Et2O—64 μL). The mixture was stirred at 0° C. for 30 minutes, then concentrated in vacuo. The residue was triturated with pentane to give the title compound (15 mg) as a white solid.

$^1$H-NMR (d$_6$-DMSO—70° C.): δ (ppm) 9.5–8.5 (b, 2H); 7.44 (m, 1H); 7.34 (m, 1H); 7.11 (m, 2H); 7.02 (m, 1H); 6.92 (m, 1H); 4.62 (bm, 1H); 4.6 (bd, 1H); 4.32 (d, 1H); 3.7–2.9 (m, 6H); 2.74 (bs, 3H); 2.33 (bs, 3H). MS (ES/+): m/z=410 [M+H—HCl]$^+$.

EXAMPLE 17

(+/−) 1-(4-Fluoro-2-methyl-phenyl)-piperazine-2-carboxylic acid (3-fluoro-5-trifluoromethyl-benzyl)-methylamide hydrochloride TFA (2.5 mL) was added to a solution of intermediate 27 (60 mg) in anhydrous DCM (15 mL) previously cooled to 0° C. under a Nitrogen atmosphere. The solution was stirred at 0° C. for 4 hours, then it was concentrated in vacuo. The residue was diluted with a saturated sodium hydrogen carbonate solution and extracted with AcOEt. The organic layer was dried and concentrated in vacuo to a residue which was purified by flash chromatography (from DCM 100% to DCM/MeOH 9:1) to give 1-(4-fluoro-2-methyl-phenyl)-piperazine-2-carboxylic acid (3-fluoro-5-trifluoromethyl-benzyl)-methylamide (33 mg). This material (33 mg) was dissolved in anhydrous Et2O (1 mL) and treated at 0° C. with hydrochloric acid (1M in Et2O —93 μL). The mixture was stirred at 0° C. for 30 minutes, then concentrated in vacuo. The residue was triturated with Et2O/pentane to give the title compound (12.7 mg) as a whitish solid.

$^1$H-NMR (d$_6$-DMSO—70° C.): δ (ppm) 9.18 (bs, 1H); 8.62 (bs, 1H); 7.49 (bd, 1H); 7.33 (bs, 1H); 7.02 (m, 2H); 6.81 (m, 2H); 4.68 (d, 1H); 4.54 (m, 1H); 4.29 (d, 1H); 3.44 (m, 3H); 3.32 (m, 2H); 2.96 (m, 1H); 2.69 (s, 3H); 2.31 (s, 3H).
MS (ES/+): m/z=428 [M+H—HCl]$^+$.

EXAMPLE 18

(+/−) 1-(2,4-Difluoro-phenyl)-piperazine-2-carboxylic acid (3,5-dichloro-benzyl)-methylamide hydrochloride TFA (1 mL) was dropped into a solution of intermediate 34 (93 mg) in anhydrous DCM (9 mL) previously cooled to 0° C. under a Nitrogen atmosphere. The solution was stirred at 0° C. overnight, then it was concentrated in vacuo. The residue was diluted with AcOEt and washed with a saturated potassium carbonate solution. The aqueous layer was extracted with further AcOEt. The combined organic extracts were washed with brine, dried and concentrated in vacuo to a residue which was purified by flash chromatography (DCM/MeOH 95:5) to give 1-(2,4difuoro-phenyl)-piperazine-2-carboxylic acid (3,5-dichlorobenzyl)-methylamide (42.8 mg).

This material (42 mg) was dissolved in anhydrous Et2O (1 mL) and treated at −10° C. with hydrochloric acid (1M in Et2O—0.1 mL). The mixture was stirred at −10° C. for 30 minutes, then concentrated in vacuo. The residue was triturated with pentane (3×2 mL) to give the title compound (38.9 mg) as a whitish solid.

$^1$H-NMR (d$_6$-DMSO—70° C.): δ (ppm) 9.19 (bs, 2H); 7.42 (s, 1H); 7.06 (s, 2H); 7.17–6.92 (m, 3H); 4.81 (m, 1H); 4.7–4.18 (m, 2H); 3.56 (m, 1H); 3.38 (m, 2H); 3.26 (m, 2H); 2.83 (m, 1H); 2.83 (s, 3H). MS (ES/+): m/z=414 [M+H—HCl]$^+$.

EXAMPLE 19

(+/−) 1-(2,4-Difluoro-phenyl)-piperazine-2-carboxylic acid (3,5-bis-trifluoromethyl-benzyl)-methylamide hydrochloride TFA (1 mL) was dropped into a solution of intermediate 35 (115 mg) in anhydrous DCM (9 mL) previously cooled to 0° C. under a Nitrogen atmosphere. The solution was stirred at 0° C. overnight, then it was concentrated in vacuo. The residue was diluted with AcOEt and washed with a saturated potassium carbonate solution. The aqueous layer was extracted with further AcOEt. The combined organic extracts were washed with brine, dried and concentrated in vacuo to a residue which was purified by flash chromatography (DCM/MeOH 95:5) to give 1-(2,4-difluoro-phenyl)-piperazine-2-carboxylic acid (3,5-bis-trifluoromethyl-benzyl)-methylamide (46 mg).

This material (46 mg) was dissolved in anhydrous Et2O (1 mL) and treated at −10° C. with hydrochloric acid (1M in Et2O—0.1 mL). The mixture was stirred at −10° C. for 30 minutes, then concentrated in vacuo. The residue was triturated with pentane (3×2 mL) to give the title compound (45 mg) as a whitish solid.

$^1$H-NMR (d$_6$-DMSO—70° C.): δ (ppm) 10–8.4 (2bs, 2H); 7.93 (s, 1H); 7.76 (s, 2H); 7.2–6.84 (m, 3H); 4.84 (m, 1H); 4.7–4.3 (dd, 2H); 3.6–3.0 (m, 6H); 2.86 (s, 3H). MS (ES/+): m/z=482 [M+H—HCl]$^+$.

EXAMPLE 20

(+/−) 1-(2,4,6-Trifluoro-phenyl)-piperazine-2-carboxylic acid (3,5-dichloro-benzyl)-methylamide hydrochloride TFA (0.5 mL) was dropped into a solution of intermediate 42 (25 mg) in anhydrous DCM (4 mL) previously cooled to 0° C. under a Nitrogen atmosphere. The solution was stirred at 0° C. overnight, then it was concentrated in vacuo. The residue was diluted with AcOEt and washed with a saturated potassium carbonate solution. The aqueous layer was extracted with further AcOEt. The combined organic extracts were washed with brine, dried and concentrated in vacuo to a residue which was purified by flash chromatography (DCM/MeOH 9:1) to give 1-(2,4,6-trifluoro-phenyl)-piperazine-2-carboxylic acid (3,5-dichlorobenzyl)-methylamide (10.3 mg).

This material (10.3 mg) was dissolved in anhydrous Et2O (0.8 mL) and treated at −10° C. with hydrochloric acid (1M in Et2O—30 μL). The mixture was stirred at −10° C. for 15 minutes, then concentrated in vacuo. The residue was triturated with pentane (3×2 mL) to give the title compound (11.9 mg) as a whitish solid.

$^1$H-NMR (d$_6$-DMSO—70° C.): δ (ppm) 9.3–8.4 (2bs, 2H); 7.45 (s, 1H); 7.2 (s, 2H); 7.0 (s, 2H); 4.72 (bm, 1H); 4.65 (d, 1H); 4.21 (d, 1H); 3.5–3.3 (m, 6H); 2.86 (s, 3H). MS (ES/+): m/z=432 [M+H—HCl]$^+$.

EXAMPLE 21

(+/−) 1-(2,4,6-Trifluoro-phenyl)-piperazine-2-carboxylic acid (3,5-bis-trifluoromethyl-benzyl)-methylamide hydrochloride TFA (0.5 mL) was dropped into a solution of intermediate 43 (31 mg) in anhydrous DCM (5 mL) previously cooled to 0° C. under a Nitrogen atmosphere. The solution was stirred at 0° C. overnight, then for TFA (0.2 mL) was added and the solution was stirred at 0° C. for further 2 hours. The solution was concentrated in vacuo. The residue was diluted with AcOEt and washed with a saturated potassium carbonate solution. The aqueous layer was extracted with further AcOEt. The combined organic extracts were washed with brine, dried and concentrated in vacuo to a residue which was purified by flash chromatography (DCM/MeOH 98:2) to give 1-(2,4,-trifluoro-phenyl)-piperazine-2-carboxylic acid (3,5-bis-trifluoromethyl-benzyl)-methylamide (18.1 mg).

This material (18.1 mg) was dissolved in anhydrous Et2O (1 mL) and treated at −10° C. with hydrochloric acid (1M in Et2O—0.08 mL). The mixture was stirred at −10° C. for 15 minutes, then concentrated in vacuo. The residue was triturated with pentane to give the title compound (10 mg) as a whitish solid.

$^1$H-NMR (d$_6$-DMSO—70° C.): δ (ppm) 8.6–8.3 (2bs, 2H); 7.94 (s, 1H); 7.78 (s, 2H); 6.95 (t, 2H); 4.84 (bd, 1H); 4.67 (bt, 2H); 4.4 (bd, 1H); 3.5–3.1 (m, 6H); 2.86 (s, 3H). MS (ES/+): m/z=500 [M+H—HCl]$^+$.

EXAMPLE 22

(+/−) 1-(4-Fluoro-phenyl)-piperazine-2-carboxylic acid (3,5-bis-trifluoromethyl-benzyl)-methylamide hydrochloride A mixture of intermediate 47 (77 mg) in EtOH (10 mL) containing 2 drops of glacial acetic acid and 10% palladium on carbon (20 mg) was stirred under hydrogen at 6 atmospheres for 22 hours. The mixture was filtered through a pad of celite. Concentration in vacuo gave a crude which was purified by flash chromatography (AcOEt/MeOH 9:1) to give 1-(4-fluoro-phenyl)-piperazine-2-carboxylic acid, (3,5-bis-trifluoromethyl-benzyl)-methylamide (44 mg). This material (44 mg) was dissolved in anhydrous Et2O (3 mL) and treated at 0° C. with hydrochloric acid (1M in Et2O—114 μL). The mixture was stirred at 0° C. for 15 minutes, then concentrated in vacuo. The residue was triturated with pentane to give the title compound (35 mg) as a whitish solid.

$^1$H-NMR (d$_6$-DMSO): δ (ppm) 9.6–9.4 (bs, 1H); 8.4–8.2 (bs, 1H); 8.02 (s, 1H); 7.79–7.62 (2s, 1H); 7.05–6.8 (m+dd, 2H); 5.27 (2s, 1H); 4.91–4.64 (2d, 1H); 4.64–4.41 (2d, 1H); 3.6–3.06 (m, 6H); 2.94–2.85 (2s, 3H). MS (ES/+): m/z=464 [M-HCl+H]$^+$.

EXAMPLE 23

(+/−) 1-(4-Fluoro-phenyl)-piperazine-2-carboxylic acid (3,5-dichloro-benzyl)-methylamide hydrochloride TFA (2 mL) was dropped into a solution of intermediate 51 (65 mg) in anhydrous DCM (10 mL) previously cooled to 0° C. under a Nitrogen atmosphere. The solution was stirred at 0° C. overnight, then it was concentrated in vacuo. The residue was diluted with AcOEt and washed with a saturated sodium carbonate solution. The aqueous layer was extracted with further AcOEt. The combined organic extracts were washed with brine, dried and concentrated in vacuo to a residue which was purified by flash chromatography (DCM/MeOH 9:1) to give 1-(4-fluoro-phenyl)-piperazine-2-carboxylic acid (3,5-dichlorobenzyl)-methylamide (15 mg). This material (15 mg) was dissolved in anhydrous Et2O (1 mL) and treated at 0° C. with hydrochloric acid (1M in Et2O—42 µL). The mixture was stirred at 0° C. for 15 minutes, then concentrated in vacuo. The residue was triturated with pentane to give the title compound (11.9 mg) as a whitish solid.

$^1$H-NMR (d$_6$-DMSO): δ ppm) 9.42 (bs, 1H); 8.25 (bs, 1H); 7.48 (s, 1H); 7.15–6.8 (m, 6H); 5.14 (m, 1H); 4.68 (d, 1H); 4.26 (d, 1H); 3.6–3.0 (m, 6H); 2.87 (s, 3H); MS (ES/+): m/z=396 [M+H—HCl]$^+$.

EXAMPLE 24

(+/−) 1-(4-Trifluoro-phenyl)-piperazine-2-carboxylic acid (3,5-dichloro-benzyl)-methylamide hydrochloride TFA (1 mL) was dropped into a solution of intermediate 58 (60 mg) in anhydrous DCM (4.5 mL) previously cooled to 0° C. under a Nitrogen atmosphere. The solution was stirred at 0° C. for 16 hours, then it was diluted with a saturated sodium carbonate solution and extracted twice with AcOEt. The combined organic extracts were dried and concentrated in vacuo to a residue which was purified by flash chromatography (DCM/MeOH 9:1) to give 1-(4-trifluoromethyl-phenyl)-piperazine-2-carboxylic acid (3,5-dichlorobenzyl)-methylamide (45 mg—T.l.c.: DCM/MeOH 9:1, Rf=0.34).

This material (45 mg) was dissolved in anhydrous Et2O (1 mL) and AcOEt (2 mL) and treated at −5° C. with hydrochloric acid (1M in Et2O—110 µL). The mixture was stirred at 0° C. for 30 minutes, then concentrated in vacuo. The residue was triturated with pentane to give the title compound (25.1 mg).

$^1$H-NMR (d$_6$-DMSO): δ (ppm) 9.82 (bs, 1H); 8.32 (bs, 1H); 7.7–6.9 (m+m, 7H); 5.44 (s, 1H); 4.73 (d, 1H); 4.32 (d, 1H); 4.14–3.0 (m, 6H); 2.99–2.83 (s+s, 3H). MS (ES/+): m/z=445 [M+H—HCl]$^+$.

EXAMPLE 25

(+/−) 1-(4-Trifluoromethyl-phenyl)-piperazine-2-carboxylic acid (3,5-bis-trifluoromethyl-benzyl)-methylamide hydrochloride TFA (1 mL) was dropped into a solution of intermediate 59 (70 mg) in anhydrous DCM (4.5 mL) previously cooled to 0° C. under a Nitrogen atmosphere. The solution was stirred at 0° C. for 16 hours, then it was diluted with a saturated sodium carbonate solution and extracted twice with AcOEt. The combined organic extracts were dried and concentrated in vacuo to a residue which was purified by flash chromatography (DCM/MeOH 9:1) to give 1-(4-trifluoromethyl-phenyl)-piperazine-2-carboxylic acid (3,5-bis-trifluoromethybenzyl)-methylamide (54 mg—T.l.c.: DCM/MeOH 9:1, Rf=0.39).

This material (54 mg) was dissolved in anhydrous Et2O (1.6 mL) and treated at −5° C. with hydrochloric acid (1M in Et2O—115 µL). The mixture was stirred at 0° C. for 30 minutes, then concentrated in vacuo. The residue was triturated with pentane to give the title compound (36 mg).

$^1$H-NMR (d$_6$-DMSO): δ (ppm) 9.7 (bs, 1H); 8.3 (bs, 1H); 7.99–7.95 (s+s, 1H); 7.81–7.55 (s +s, 2H); 7.54–7.37 (d+d, 2H); 7.13–6.85 (d+d, 2H); 5.44–5.52 (s+s, 1H); 4.97–4.73 (d+d, 1H); 4.61–4.41 (d+d, 1H); 3.9–3.0 (m, 6H); 3.03–2.92 (s+s, 3H). MS (ES/+): m/z=513 [M+H—HCl]$^+$.

EXAMPLE 26

(+/−) 1-(4-Fluoro-2-methyl-phenyl)-piperazine-2-carboxylic acid, (3,5-dichloro-benzyl)-methylamide as a Crystalline form Example 2a (1 g) was suspended in MeOH (12 mL) and heated to 65–70° C. until completed dissolution. The mixture was cooled to 50° C. then it was filtered and concentrated to 10 mL. The resulting solution was cooled again to 20° C. and 0.005 g of example 2a seed was added. The solution was stirred over two hours before the slow (1 hour) addition of water (7.5 mL). The solid was stirred at 20° C. for 16–18 hours. The following day the solid was filtered and washed with MeOH/H2O 6/4 (3 mL). It was dried in vacuum at 40° C. for 18 hours to obtain the title compound (0.9 g); mp 169.97° C.

X ray powder diffraction data are reported in table 1

TABLE 1

The X-ray powder diffraction pattern of the product of Example 26 in terms of 'd' spacings is as follows

| Angle (°2θ) | d value (A) |
| --- | --- |
| 14,688 | 6,026 |
| 18,744 | 4,730 |
| 20,812 | 4,265 |
| 21,691 | 4,094 |
| 25,034 | 3,554 |
| 25,687 | 3,465 |
| 25,933 | 3,433 |
| 28,072 | 3,176 |

PHARMACY EXAMPLES

A. Capsules/Tablets

| | |
| --- | --- |
| Active ingredient | 25.0 mg |
| PYP | 2.5 mg |
| Microcrystalline Cellulose | 198.5 mg |
| Croscarmellose Sodium | 2.5 mg |
| Magnesium Stearate | 1.5 mg |

The active ingredient is blended with the other excipients. The blend can be used to fill gelatin capsules or compressed to form tablets using appropriate punches. The tablets can be coated using conventional techniques and coatings.

B. Tablets

| | |
| --- | --- |
| Active ingredient | 25.0 mg |
| Microcrystalline Cellulose | 264.0 mg |
| Croscarmellose Sodium | 10.0 mg |
| Magnesium Stearate | 1.0 mg |

The active ingredient is blended with microcrystalline cellulose and croscarmellose sodium. Magnesium stearate is then added to the previuos blend. The mixture thus obtained can be compressed using appropriate punches and the tablets coated using conventional techniques and coatings.

C) Infusion

| | |
|---|---|
| Active ingredient | 2-50 mg/ml |
| Buffer solution pH 4.5 suitable for infusion (e.g. sodium citrate in NaCl 0.9% or 5% dextrose) | qs to 100 ml |

The formulation may be packed in glass vials or plastic bag.

The affinity of the compound of the invention for $NK_1$ receptor was determined using the $NK_1$ receptor binding affinity method measuring in vitro by the compounds' ability to displace [3H]—substance P (SP) from recombinant human $NK_1$ receptors expressed in Chinese Hamster Ovary (CHO) cell membranes. The affinity values are expressed as negative logarithm of the inhibition constant (Ki) of displacer ligands (pKi).

The pKi values obtained as the average of at least two determinations with representative compounds of the invention are within the range of 9.40 to 8.00.

The affinity of the compound of the invention for serotonin transporter was determined using the hSERT binding affinity method and measuring in vitro the compounds' ability to displace [3H]—Imipramine from recombinant human serotonin transporter expressed in Human Embryonic Kidney HEK293 cell membranes. The affinity values are expressed as negative logarithm of the inhibition constant (Ki) of displacer ligands (pKi).

The pKi values obtained as the average of at least two determinations with representative compounds of the invention are within the range of 6.31 to 8.95.

The invention claimed is:

1. A compound of formula (I)

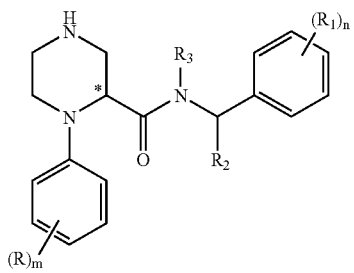

wherein
R represents halogen, $C_{1-4}$ alkyl, trifluommethoxy or trifluoromethyl;
$R_1$ is trifluoromethyl, $C_{1-4}$ alkyl, $C_{1-4}$ alkoxy, halogen or trifluoromethoxy;
$R_2$ is hydrogen, $C_{1-4}$ alkyl or $C_{2-6}$ alkenyl;
$R_3$ represents hydrogen or $C_{1-4}$ alkyl;
n and m are independently 0 or an integer from 1 to 3;
or a pharmaceutically acceptable salt or hydrate thereof.

2. A compound as claimed in claim 1 wherein $R_1$ is trifluoromethyl or halogen and n is 2.

3. A compound as claimed in claim 1 wherein R is selected from triflluromethyl, methyl or halogen, $R_1$ is trifluoromethyl or halogen and n is 2, $R_3$ is methyl, $R_2$ is methyl or hydrogen.

4. A compound selected from
(+/−)1-(4-Fluoro-2-methyl-phenyl)-piperazine-2-carboxylic acid (3,5-dichloro-benzyl)-methylamide;
(+)1-(4-Fluoro-2-methyl-phenyl)-piperazine-2-carboxylic acid (3,5-dichloro-benzyl)-methylamide;
(−)1-(4-Fluoro-2-methyl-phenyl)-piperazine-2-carboxylic acid (3,5-dichloro-benzyl)-methylamide;
and amorphous and crystalline forms thereof and pharmaceutically acceptable salts thereof.

5. A compound selected from:
(+/−)1-(4-Fluoro-2-methyl-phenyl)-piperazine-2-carboxylic acid, (3,5-bis-trifluoromethyl-benzyl)-methylamide;
(+/−)1-(4-Fluoro-2-methyl-phenyl)-piperazine-2-carboxylic acid (3,5-dichloro-benzyl)-methylamide;
(+/−)1-(4-Fluoro-2-methyl-phenyl)-piperazine-2-carboxylic acid [1-(3,5-dichloro-phenyl)-ethyl]-methylamide;
(+/−)1-(4-Fluoro-2-methyl-phenyl)-piperazine-2-carboxylic acid (3,5-bis-trifluoromethyl-benzyl)-methylamide;
(+/−)1-(4-Fluoro-2-methyl-phenyl)-piperazine-2-carboxylic acid (3,4-dibromo-benzyl)-methylamide;
(+/−)1-(4-Trifluoromethyl-phenyl)-piperazine-2-carboxylic acid (3,5-bis-trifluoromethyl-benzyl)-methylamide;
and pharmaceutically acceptable salts and hydrates thereof.

6. A pharmaceutical composition comprising a compound as claimed in claim 1 in admixture with one or more pharmaceutically acceptable carriers or excipients.

7. A process for the preparation of a compound as claimed in claim 1, which comprises reacting an activated derivative of the carboxylic acid of formula (II) or an enantiomer thereof, with amine (III),

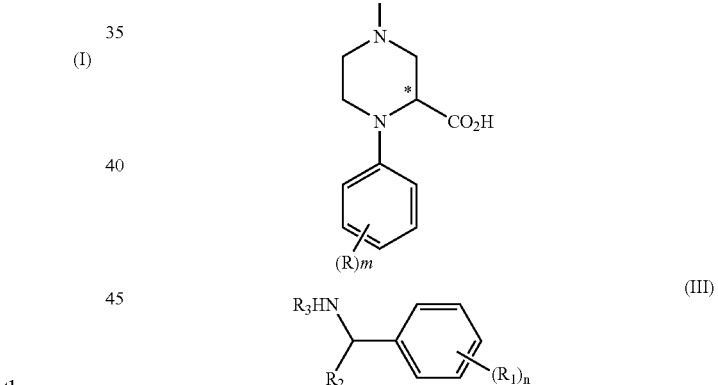

wherein $R_a$ is a suitable nitrogen protecting group;
followed where necessary or desired by one or more of the following steps
1. removal of any protecting group;
2. isolation of the compound as a salt or a hydrate thereof;
3. separation of a compound of formula(I) or derivative thereof into the enantiomers thereof.

8. A method for the treatment of depression in a mammal in need thereof, said method comprising administering an effective amount of a compound as claimed in claim 1.

9. The method according to claim 8, wherein said mammal is man.

10. A method for the treatment of anxiety in a mammal in need thereof, said method comprising administering an effective amount of a compound as claimed in claim 1.

11. The method according to claim 10, wherein said mammal is man.

12. A method for the treatment of both depression and anxiety in a mammal in need thereof, said method comprising administering an effective amount of a compound as claimed in claim 1.

13. The method according to claim 12, wherein said mammal is man.

14. A compound selected from
(+/−)1-(4-Fluoro-2-methyl-phenyl)-piperazine-2-carboxylic acid (3,5-dichloro-benzyl)-methylamide hydrochloride;
(+)1-(4-Fluoro-2-methyl-phenyl)-piperazine-2-carboxylic acid (3,5-dichloro-benzyl)-methylamide hydrochloride; and
(−)1-(4-Fluoro-2-methyl-phenyl)-piperazine-2-carboxylic acid (3,5-dichloro-benzyl)-methylamide hydrochloride.

15. A compound selected from:
(+/−)1-(4-Fluoro-2-methyl-phenyl)-piperazine-2-carboxylic acid, (3,5-bis-trifluoromethyl-benzyl)-methylamide hydrochloride;
(+/−)1-(4-Fluoro-2-methyl-phenyl)-piperazine-2-carboxylic acid (3,5-dichloro-benzyl)-methylamide hydrochloride;
(+/−)1-(4-Fluoro-2-methyl-phenyl)-piperazine-2-carboxylic acid [1-(3,5-dichloro-phenyl)-ethyl]-methylamide hydrochloride;
(+/−)1-(4-Fluoro-2-methyl-phenyl)-piperazine-2-carboxylic acid (3,5-bis-trifluoromethyl-benzyl)-methylamide hydrochloride;
(+/−)1-(4-Fluoro-2-methyl-phenyl)-piperazine-2-carboxylic acid (3,4-dibromo-benzyl)-methylamide hydrochloride; and
(+/−)1-(4-Trifluoromethyl-phenyl)-piperazine-2-carboxylic acid (3,5-bis-trifluoromethyl-benzyl)-methylamide hydrochloride.

* * * * *

UNITED STATES PATENT AND TRADEMARK OFFICE
CERTIFICATE OF CORRECTION

| | | |
|---|---|---|
| PATENT NO. | : 7,214,680 B2 | Page 1 of 1 |
| APPLICATION NO. | : 10/486479 | |
| DATED | : May 8, 2007 | |
| INVENTOR(S) | : Alvaro et al. | |

It is certified that error appears in the above-identified patent and that said Letters Patent is hereby corrected as shown below:

Title Page, item (57) Abstract should read:
--The present invention relates to piperazine derivatives of formula (I) --

Column 51, Claim 1, line 49 should read:
-- R represents halogen, $C_{1-4}$ alkyl, trifluoromethoxy or --

Column 51, Claim 3, line 60 should read:
--selected from trifluoromethyl, methyl or halogen, R1 is tri- --

Signed and Sealed this

Twenty-third Day of October, 2007

JON W. DUDAS
*Director of the United States Patent and Trademark Office*